(12) United States Patent
Morrison et al.

(10) Patent No.: US 6,284,536 B1
(45) Date of Patent: Sep. 4, 2001

(54) MODIFIED IMMUNOGLOBIN MOLECULES AND METHODS FOR USE THEREOF

(75) Inventors: Sherie L. Morrison; Koteswara R. Chintalacharuvu, both of Los Angeles; Esther Mikyung Yoo, Thousand Oaks; Kham M. Trinh, Monterey Park; M. Josefina Coloma, Santa Monica, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/295,283

(22) Filed: Apr. 20, 1999

Related U.S. Application Data

(60) Provisional application No. 60/096,085, filed on Aug. 11, 1998, and provisional application No. 60/082,578, filed on Apr. 20, 1998.

(51) Int. Cl.[7] .............................. C12N 5/06; C12Q 1/70; G01N 33/53; A61K 39/395; C12P 21/08
(52) U.S. Cl. .............................. 435/328; 435/5; 435/7.1; 435/69.7; 435/70.1; 435/320.1; 435/339.1; 530/387.3; 536/23.43; 424/133.1; 424/160.1; 424/161.1
(58) Field of Search .............................. 435/5, 7.1, 320.1, 435/339.1, 69.7, 70.1, 328; 530/387.3; 536/23.43; 424/133.1, 160.1, 161.1

(56) References Cited

FOREIGN PATENT DOCUMENTS

WO 89/07142  1/1989  (WO).
WO 97/42313  11/1997 (WO).

OTHER PUBLICATIONS

Atkin, J.D. et al., "Mutagenesis of the Human IgA1 Heavy Chain Tailpiece That Prevents Dimer Assembly[1]", Jul. 1, 1996, J. Immunol., 157(1):156–159.

Boulianne et al., "Production of Functional Chimaeric Mouse/Human Antibody", Dec. 13, 1984, Nature, 312:643.

Carayannopoulos, L. et al., "Localization of the Binding Site for the Monocyte Immunoglobulin (Ig) A–Fc Receptor (CD89) to the Domain Boundary Between Cα and Cα3 in Human IgA1", Apr. 1996, J. Exp. Med., 183:1579–1586.

Chintalacharuvu and Morrison, "Residues Critical for H–L Disulfide Bond Formation in Human IgA1 and IgA2[1]", Oct. 15, 1996, J. Immunol., 157:3443–49.

Krugmann, S. et al., "Mutagenesis of J Chain Residues Critical for IgA Dimer Assembly", May 1997, Biochem. Soc. Trans 25(2):323S.

Morrison et al., "Chimeric Human Antibody Molecules: Mouse Antigen–binding Domains with Human Constant Region Domains", Nov. 1984, PNAS, USA, 81:6851–6855.

(List continued on next page.)

*Primary Examiner*—Hankyel T. Park
(74) *Attorney, Agent, or Firm*—Gates & Cooper LL

(57) ABSTRACT

Disclosed are modified immunoglobulin (Ig) molecules, a method of producing modified Ig molecules, and methods for treatment and prevention of infectious diseases using modified Ig molecules. In one embodiment, the modified Ig molecule comprises a $C_H3$ domain of an IgA molecule (α $C_H3$). The combination of an α $C_H3$ with other domains selected from one or more nonIgA Ig molecules provides an Ig molecule that has the capacity to bind J chain and/or secretory component (SC) together with features of a nonIgA molecule. In another embodiment, the modified Ig molecule comprises a $C_H1$ and/or a $C_H2$ domain of an IgA molecule. The combination of an α $C_H1$ and/or $C_H2$ domain with other domains selected from one or more nonIgA Ig molecules provides an Ig molecule that has the capacity to form higher polymers (trimers, tetramers, pentamers, etc.) together with features of a nonIgA molecule. In one embodiment, the modified immunoglobulin molecule lacks one or more carbohydrate addition sites.

31 Claims, 11 Drawing Sheets

OTHER PUBLICATIONS

Neuberger et al., "A Hapten–specific Chimeric IgE Antibody with Human Physiological Effector Function", Mar. 1985 Nature, 314:268–270.

Niles, M.J. et al., "Polymer IgM Assembly and Secretion in Lymphoid and Nonlymphoid Cell Lines: Evidence that J Chain is required for Pentamer IgM Synthesis", Mar. 1995, Proc. Natl., Acad. Sci., USA, 92:2884–2888.

Wiersma, E.J. et al., "Analysis of IgM Structures Involved in J Chain Incorporation[1]", Feb. 15, 1997, J. Immunol. 158(4):1719–1726.

Ma, Julian K.C. et al., "Generation and Assembly of Secretory Antibodies in Plants," Science, May 5, 1995, vol. 268, pp. 716–719.

Sorensen, Vigdis et al., "Effect of the IgM and IgA Secretory Tailpieces on Polymerization and Secretion of IgM and IgG," Journal of Immunology, 1996, 156: 2858–2865.

Smith, Richard I.F. et al., "Addition of a $\mu$–Tailpiece to IgG Results in Polymeric Antibodies with Enhanced Effector Functions Including Complement–Mediated Cytolysis by IgG4," Journal of Immunology, 1995, 154: 2226–2236.

Clarke, R.A. et al., "Expression of a Recombinant Sheep IgE Gene," Immunological Investigation, 1994, 23(1), 25–37.

MODIFIED IMMUNOGLOBIN MOLECULES AND METHODS FOR USE THEREOF

This application claims the benefit of U.S. provisional patent application Ser. Nos. 60/082,578, filed Apr. 20, 1998, and 60/096,085, filed Aug. 11, 1998. The entire contents of each of these provisional patent applications are incorporated by reference into this application.

This invention was made with Government support under Grant Nos. AI29470-1, AI29470-2, AI39187-1, AI39187-2, CA 16858-1 and CA 16858-2, awarded by the National Institutes of Health. The government has certain rights in this invention.

Throughout this application various publications are referenced. The disclosures of these publications in their entireties are hereby incorporated by reference into this application in order to more fully describe the state of the art to which this invention pertains.

TECHNICAL FIELD OF THE INVENTION

The invention relates to modified immunoglobulin molecules comprising at least a portion of a domain of an immunoglobulin (Ig) of a first class and at least a portion of an immunoglobulin of a second class. In a preferred embodiment, the first Ig is of the IgA class. The domain of the Ig molecule is typically a constant domain. Modified Ig molecules comprising portions of different immunoglobulin classes can be used in the diagnosis, prevention and treatment of infection and other diseases.

BACKGROUND OF THE INVENTION

The design of modified immunoglobulin molecules makes it possible to overcome the limitations of naturally-occurring antibodies. Chimeric antibodies having an antigen-binding region derived from a murine source and constant regions of human origin are described, for example, in Neuberger et al., 1985, Nature 314:268–270; and Bouhanne et al., 1984, Nature 312:643. Antibodies having constant regions modified to contain domains of different IgG isotypes are described in WO 89/07142.

There remains a need for immunoglobulin molecules offering desired features characteristic of one Ig class in combination with desired features characteristic of another Ig class. In addition, information about which domains of Ig molecules confer the desired features is needed to guide in the design of modified Ig molecules.

SUMMARY OF THE INVENTION

The invention provides a modified immunoglobulin molecule comprising a constant domain of an IgA molecule, and at least a portion of a nonIgA immunoglobulin molecule. In one embodiment, the constant domain is a $C_H1$, $C_H2$ and/or $C_H3$ domain. In one embodiment, the portion of a nonIgA immunoglobulin molecule comprises a $C_H2$ domain. The nonIgA immunoglobulin molecule can be an IgG, IgM, IgE, or IgD molecule. In one embodiment, the modified Ig molecule further comprises a tail-piece region of an IgA immunoglobulin molecule, a J chain, and/or secretory component (SC).

The invention additionally provides polynucleotides encoding a modified immunoglobulin molecule, vectors and host cells which can be used in a method of producing a modified immunoglobulin molecule.

The invention also provides a pharmaceutical composition comprising the modified immunoglobulin molecule and, optionally, a pharmaceutically acceptable carrier. The composition can be used in a method of treating or preventing an infection in a subject. The method comprises administering the composition to the subject. The infection to be treated or prevented can be systemic, local, or at a mucosal surface.

DETAILED DESCRIPTION

Figures 1A, 1B:
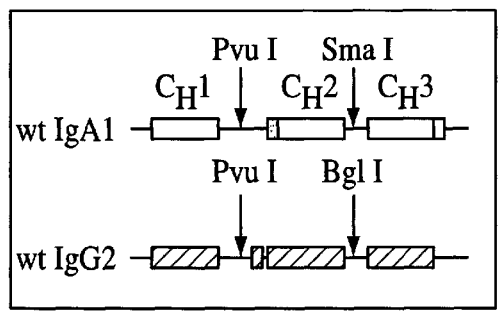
FIG. 1A is a schematic diagram of H chain constant region genes, showing where unique Pvu I restriction sites were introduced between the $C_H1$ and $C_H2$ of α1 and γ2.
FIG. 1B is a schematic diagram showing wild type α1, γ2, and the six possible domain exchanged constructs (#s 1–6). In addition, wild type γ2 and constructs 4–6 were constructed with αtp. The domain composition of the antibodies was confirmed by ELISA using antigen coated microtiter plates and P specific (HP6053), Cγ1 specific (HP6014), Cγ2 specific (HP6002) and Cγ3 specific antibodies (HP6017) as detecting antibodies.

The present invention provides modified immunoglobulin (Ig) molecules, methods of producing modified Ig molecules, and methods for diagnosis, treatment and prevention of infectious and other diseases using modified Ig molecules. The modified Ig molecules comprise portions of Ig molecules of different Ig classes, such as IgA, IgG, IgM, IgD and IgE. In one embodiment, the modified Ig molecule comprises a C$_H$3 domain of an IgA molecule (α C$_H$3 or Cα3). The combination of an α C$_H$3 with other domains selected from one or more nonIgA Ig molecules provides an Ig molecule that has the capacity to bind J chain and/or secretory component (SC) together with features of a nonIgA molecule. In another embodiment, the modified Ig molecule comprises a C$_H$1 and/or a C$_H$2 domain of an IgA molecule. The combination of an α C$_H$1 and/or C$_H$2 domain with other domains selected from one or more nonIgA Ig molecules provides an Ig molecule that has the capacity to form higher polymers (trimers, tetramers, pentamers, etc.) together with features of a nonIgA molecule. The modified Ig can further include an α or μ tail piece. The presence of the tail piece facilitates the formation of dimers and higher polymers.

Definitions

All scientific and technical terms used in this application have meanings commonly used in the art unless otherwise specified. As used in this application, the following words or phrases have the meanings specified.

As used herein, "modified Ig molecule" means an immunoglobulin ("Ig") molecule that differs from a naturally-occurring Ig molecule by containing at least a portion of two or more Ig molecules of differing Ig classes. A modified Ig molecule can be made, for example, by conventional genetic recombination using polynucleotides encoding Ig domains or portions thereof arranged in a chosen array and expressed in a cell. Alternatively, a modified Ig molecule can be synthesized using conventional techniques of polypeptide synthesis. The Ig molecule can be an IgA, IgM, IgG, IgD, or IgE molecule. IgA includes IgA1 and IgA2.

As used herein, "constant region domain" or "constant domain" refers to a domain within the constant portion of an Ig molecule, including $C_L$, $C_H1$, hinge, $C_H2$, $C_H3$ and $C_H4$.

As used herein, a "variable region domain" or "variable domain" refers to that portion of an Ig molecule which confers specificity of the Ig for a particular antigen.

As used herein, "tail-piece" or "tp" means a peptide located at the free carboxyl end of an immunoglobulin heavy chain. A tail-piece comprises an amino acid sequence which may vary in length from about 15 to about 21 amino acids, but which is typically about 18 amino acids long.

As used herein, "secretory component" or "SC" means a protein fragment corresponding to the ectoplasmic domain of an IgA receptor. (The domains of SC are described in J. F. Piskurich, et al., 1995, J. Immunol. 154: 1735–1747.) In preferred embodiments, the SC is derived from a human or other mammal.

As used herein, "antigen" means a substance capable of either binding to an antigen binding region of an immunoglobulin molecule or of eliciting an immune response. As used herein, "antigen" includes, but is not limited to, antigenic determinants, haptens, and immunogens.

As used herein, "vector" means a construct which is capable of delivering, and preferably expressing, one or more genes or polynucleotide sequences of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eucaryotic cells, such as producer cells.

As used herein, "polynucleotide" or "nucleic acid" means a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Unless otherwise indicated, a particular nucleic acid sequence optionally includes the complementary sequence. The polynucleotide sequence may encode variable and/or constant region domains of immunoglobulin.

As used herein, "pharmaceutically acceptable carrier" includes any material which, when combined with an Ig, allows the Ig to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration include phosphate buffered saline or normal (0.85%) saline.

As used in the appended claims, "a" means at least one, and can include a plurality.

Modified Immunoglobulin Molecule

The present invention provides a modified immunoglobulin molecule comprising a constant domain of an IgA molecule, and at least a portion of a nonIgA immunoglobulin molecule. Examples of a constant domain of an IgA molecule include, but are not limited to, $C_H1$ (C$\alpha$1), hinge, $C_H2$ (C$\alpha$2), and $C_H3$ (C$\alpha$3). In a preferred embodiment, the modified Ig molecule comprises a $C_H3$ region of an IgA molecule and at least a portion of a nonIgA molecule. The IgA portion of the modified molecule can be derived from, for example, an IgA1 or IgA2 molecule. The nonIgA portion (s) of the modified Ig molecule can be derived from a molecule of another Ig class, such as IgG, IgM, IgE, IgD, or any combination thereof. The nonIgA portion of the modified molecule can include one or more parts of light and/or heavy Ig chains. Preferably, the nonIgA portion of the modified Ig molecule includes, but is not limited to, a $C_H1$, $C_H2$ or $C_H3$ domain.

In one embodiment, the domain of a nonIgA immunoglobulin molecule is derived from a nonmucosal Ig molecule, such as IgG, IgD or IgE. Selecting a domain of a nonmucosal Ig molecule, such as an IgG for example, can be used to avoid recognition by bacterial proteins such as ARP4. These bacterial proteins can otherwise escape immune attack because of their ability to bind IgA or IgM in a manner that avoids antibody binding. One example of a domain of a nonmucosal Ig molecule suitable for this purpose is C$\gamma$2.

In another embodiment, the modified Ig further comprises an antigen-binding region, examples of which include an Fv region. In another embodiment, the modified Ig includes a variable region domain and/or a constant region domain.

The modified Ig can include a heavy and light chain pair, held together by covalent or noncovalent bond forces. In another embodiment, the modified Ig molecule further comprises a $C_H2$ region of an IgA molecule. Inclusion of a C$\alpha$2 can be selected to reduce the ability of the molecule to elicit an inflammatory reaction in vivo.

As is known to those skilled in the art, constant region domains, such as hinge, $C_H2$, $C_H3$ and $C_H4$, possess functional or biological features which are characteristic of these particular domains. These constant region domains may be added to or deleted from the modified molecule, or selected from particular Ig classes and subclasses to obtain desired biological effects. For example, a $C_H2$ domain of a given Ig class may be added when complement binding activity is desired. In another example, deletion of a $C_H1$ domain from a modified Ig would permit secretion of heavy chains from cells without associated light chains. In addition, an $\alpha$ tail piece, $\mu$ tail piece, or an $\alpha/\mu$ hybrid tail piece can be added to a modified Ig molecule of the invention to facilitate formation of polymeric Ig molecules.

Domains within a modified Ig molecule of the invention can themselves be modified, for example, by having a substitution, deletion, duplication or rearrangement of substantially all of the amino acids of at least one of the domains, including modification by site-directed mutagenesis. Examples of methods useful in the preparation of domain-modified Ig molecules are described in WO 89/07142. Amino acid substitutions include, but are not necessarily limited to, amino acid substitutions known in the art as "conservative".

For example, it is a well-established principle of protein chemistry that certain amino acid substitutions, referred to as conservative amino acid substitutions, can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered conservative in particular environments.

In one embodiment, the modified Ig molecule further comprises J chain. In another embodiment, the modified Ig molecule further comprises secretory component (SC), a variant of SC or a fragment thereof.

The modified Ig can comprise variable and constant region domains from either the same or different species. Variable and constant region domains may be obtained from vertebrate and/or invertebrate animal sources. Mammalian sources include, but are not limited to, human, mouse, rat, rabbit, sheep, or goat sources. The variable and constant region domains utilized in the modified Ig may be selected from a number of naturally occurring or genetically modified domains.

Modified Ig molecules can be made which possess desired chemical properties useful in therapeutic and diagnostic applications. For example, modified Ig molecules can be created which permit attachment of a high density of therapeutic drug or radioactive isotope to the molecule. The $C_H2$ domain is particularly rich in carbohydrate moieties, which facilitates attachment of drugs or labels to the modified molecule. Multivalent modified Ig molecules comprising several antigen binding regions can also be created to permit multi-point binding to antigens with higher avidity than univalent molecules. Greater avidity of binding can provide more effective localization of Igs to tissue sites in vivo.

In one embodiment, the modified Ig molecule is modified to alter the clearance rate. For example, the carbohydrate addition site can be removed from the $C_H2$ region, the tail-piece, or both. Absence of the tail piece carbohydrate can increase the half life of polymeric Ig, whereas absence of the carbohydrate in $C_H2$ accelerates the clearance rate. In a preferred embodiment, the modified Ig molecule comprises a $\mu$ tail piece from which the carbohydrate addition site has been deleted.

Polynucleotides, Vectors and Host Cells

The invention further provides a polynucleotide that encodes a modified Ig molecule as described above. Also provided is a vector comprising the polynucleotide of the invention. Different portions or domains of an Ig molecule of the invention can be encoded on the same or multiple vectors, and one or more Ig molecules of the invention can be included in a single vector.

The invention additionally provides a host cell transfected with a vector of the invention. The cell can be a mammalian, avian, insect, reptilian, bacterial, plant or yeast cell. Examples of mammalian cells include, but are not limited to, human, rabbit, rodent (e.g., mouse, rat) and bovine cells. In preferred embodiments, the cell is a myeloma cell, a Sp2/0 cell, a chinese hamster ovary (CHO) cell, L cell, COS cell, fibroblast, MDCK cell, HT29 cell or a T84 cell.

Methods of Producing Modified Immunoglobulin Molecules

The invention provides a method of producing a modified immunoglobulin molecule. The method comprises culturing a host cell transfected with a vector, the vector comprising a polynucleotide encoding a modified Ig molecule of the invention. The method can further comprise recovering the modified Ig molecule so produced. Modified Ig molecules produced by the cultured host cell can be recovered from the culture supernatant and purified using conventional techniques.

Modified molecules produced by host cells can also contain tail-piece, secretory component (SC), and/or J chain, by using vectors which encode tail-piece, SC, and/or J chain polypeptide components. Expression vectors can be introduced into mammalian cells by methods which include, but are not limited to, calcium phosphate transfection, nuclear microinjection, DEAE-dextran transfection, bacterial protoplast fusion, and electroporation.

In one embodiment, the expression vector is a plasmid containing a polynucleotide sequence encoding part(s) of one or more constant and/or variable region domains of immunoglobulin. In another embodiment, the polynucleotide sequence is cloned using a polymerase chain reaction (PCR) method. PCR may be used to generate a number of copies of polynucleotide chains which can then be placed into an expression vector which can subsequently be used to transform a eucaryotic or procaryotic cell. The transformed cells produce modified Ig proteins from the encoded polynucleotide sequence. Those skilled in the art will appreciate that alternative cloning methods can be used. In another embodiment, immunoglobulin enhancer elements can be added to an expression vector to increase transcription of gene sequences several hundred-fold. Bacterial vectors can be used to maximize expression of polynucleotides encoding modified Ig domains in mammalian cells (e.g., murine myeloma).

Production and Expression of IgA1/nonIgA Exon Exchanged Genes

Polynucleotides encoding the desired constant region of selected IgA and nonIgA molecules can be cloned into cloning site of a vector. Restriction sites can be introduced between selected exons to permit exchange of exons between different Ig molecules. Protocols for producing IgA1/IgG2 exon exchanged genes are provided in Example 1 below.

Polynucleotide fragments containing part(s) of constant and/or variable region genes can be cloned into an expression vector containing a $V_H$ region to produce Ig molecules specific for an antigen. The expression vector can be used to transfect a host cell. Similarly, one or more expression vectors encoding tail-piece, J chain, and/or secretory component can be inserted into the host cell.

Methods of Treating or Preventing Infectious and/or Other Diseases

The invention provides a composition. The composition comprises a modified Ig molecule and, optionally, a pharmaceutically acceptable carrier. In one embodiment, the composition is a pharmaceutical composition. In another embodiment, the composition is a diagnostic composition. The carrier should be nontoxic to the subject and chemically and physiologically compatible with other ingredients in the formulation. The invention provides a method of treating or preventing infectious and/or other diseases using modified Ig molecules. The method comprises administration of the pharmaceutical composition containing the modified Ig molecules to a subject. In an embodiment, the disease is an infection. The infection can be systemic, local, and/or at a mucosal surface. Furthermore, the infection may be caused by infectious agents which include, but are not limited to, bacteria, viruses, mycoplasma, mycobacteria, yeast, fungi, or parasites. Examples of viruses include, but are not limited to, human immunodeficiency virus, hepatitis virus, respiratory syncytial virus, influenza virus and cold virues. In another embodiment, the disease is cancer. The subjects can include, but are not limited to, mammals (e.g., primates, humans), birds, reptiles, and fish.

The pharmaceutically acceptable carrier can be in the form of a solution, suspension, or solid (e.g., powder, lyophilized pellet). In one embodiment, the composition is administered to a subject (e.g., human) in a quantity sufficient to treat or prevent an infectious disease or cancer. Pharmaceutical formulations of modified Ig molecules may be purified and mixed with physiological buffers (e.g., saline) and stabilizers. Buffers which can be acceptable include phosphate or citrate. Proteins, amino acids, polysaccharides, chelating agents, salts, and surfactants may be added to formulations (e.g., albumin, gelatin, glycine, glucose, EDTA, sodium, Tween, polyethylene glycol). Sterilization of pharmaceutical preparations can be performed by membrane filtration. Pharmaceutical formulations can include microcapsules (e.g., gelatin, polymethylmethacrylate), colloidal delivery (e.g., liposomes, microemulsions), or macroemulsions. Topical formulations can include lotions, creams, ointments, pastes, or drops which may be used on skin, or in the ear, eyes, or nose. For an aerosol formulation used in inhalation administration, modified Ig molecules are mixed with a propellant (e.g., freon plus 1,2 dichlorotetrafluoroethane and difluorochloromethane) and a lubricating agent (e.g., polysorbate 85, oleic acid).

Modified Ig molecules can be administered at a mucosal surface (e.g., orally or intranasally) in an effective dose range (e.g., up to 5 mg/kg body weight). In another embodiment, the composition can be administered as an aerosol (e.g., suspension or solution) for effective delivery via inhalation to the respiratory tract. In another embodiment, the composition is administered to a subject in a dose and route of administration (e.g., mucosal surface) which acts prophylactically to prevent infection by binding to the infectious agent (e.g., virus). Systemic routes of administration may include oral, intravenous, intraperitoneal, and intramuscular administration. Local administration can include topical application of a pharmaceutical formulation to the epidermis or to other external surfaces (e.g., mouth, nose, intragastric) where there is little absorption into the circulatory system. Suitable doses for topical administration are about 0.03 to about 15 mg/kg body weight per day, preferably about 0.5 to about 1 mg/kg body weight per day. Suitable doses for parenteral and intravenous administration are designed to achieve a level of specific antibody that is approximately 1–10% of the total IgA content (approximately 2 g/L is the total IgA content of human adult serum). For adult subjects, such doses would be about 0.1 to about 10 g daily. The judgment of the treating physician can be used to adjust the dose as appropriate for individual subjects and particular Ig molecules.

The modified Ig molecules can act to inactivate the infectious agent (e.g., virus neutralization) or promote clearance of the infectious agent by the subject's host system (e.g., reticuloendothelial system). The modified Ig molecules can be used in conjunction with Fc receptor-bearing cells (e.g., monocytes), cytotoxic drugs, toxins, or radioisotopes to kill cancer cells. These molecules can also be used as immunosuppressive agents in treatment of disease (e.g., autoimmune disease).

Methods for Diagnosing Diseases Using Modified Ig Molecules

Modified Ig molecules also can be used in conjunction with attached labels (e.g., radioactive) to diagnose disease. In a preferred embodiment, nonreactive multivalent modified Ig molecules which do not fix complement or bind to Fc receptors of cells (e.g., macrophages, null cells) but which target certain cell surface or tissue markers (e.g., tumor) are administered to a subject in a pharmaceutically acceptable carrier. For example, such molecules can be visualized by conventional imaging technologies to localize tumor sites in cancer patients in vivo.

EXAMPLES

The following examples are presented to illustrate the present invention and to assist one of ordinary skill in making and using the same. The examples are not intended in any way to otherwise limit the scope of the invention.

Example 1

IgA1/IgG2 Domain Exchanged Antibodies

This Example demonstrates the preparation of mammalian cells genetically modified to secrete IgA1/IgG2 domain exhanged antibodies. Analysis of the results shows the roles of different a domains in the assembly of polymeric IgA (pIgA) and secretory IgA (sIgA). In summary, αtp was found to be sufficient for the formation of polymers, while structures in Cα3 were important for the incorporation of J chain and binding of secretory component (SC). Both Cα2 and Cα3 contributed to efficient dimer formation.

Materials and Methods

Reagents and Cells

Restriction endonucleases and molecular cloning enzymes were obtained from New England Biolabs (Beverly, Mass.), Pharmacia (Alameda, Calif.), Stratagene (La Jolla, Calif.) or Promega (Madison, Wis.). [$^{35}$S]Cysteine and [$^{35}$S]-methionine were purchased from ICN Research Products (Costa Mesa, Calif.). The Sp2/0 myeloma cells were cultured in Iscove's modified Dulbecco's medium (IMDM) containing 5% bovine calf serum (BCS) (Hyclone Laboratories, Logan, Utah). The generation of α1 and γ2 expression vectors and their expression in Sp2/0 cells was described in earlier reports (Chintalacharuvu and Morrison, 1996, J. Immunol. 157:3443–49; Morrison et al., 1984, PNAS, USA, 81:6851–6855).

Production of IgA1/IgG2 Exon Exchanged Genes

The genomic clones coding for the constant regions of IgA1 and IgG2 were cloned into the multiple cloning site of pBR322 vector where they can be conveniently modified by exon exchange. Pvu I restriction sites were introduced between $C_\alpha 1$ and $C_\alpha 2$ exons to enable exchange of exons between α1 and γ2 (FIG. 1A). The Pvu I sites in the intron separating $C_\alpha 1$ and $C_\alpha 2$ and in the ampicillin gene were used to generate α1 with $C_\gamma 1$ and $_\gamma 2$ with $C_\alpha 1$ (FIG. 1B).

Similarly, a fragment with a Bgl I site between $C_\gamma 2$ and $C_\gamma 3$ rendered blunt and a Sca I site in the ampicillin gene was exchanged with a fragment generated using the Sma I site between $C_\alpha 2$ and $C_\alpha 3$ and Sca I in the ampicillin gene to generate $C_H 3$ exon exchanged constructs. Finally, genes with exchanged $C_H 2$ exons were generated by using Pvu I sites between $C_H 1$ and $C_H 2$ and in the ampicillin gene in the wild type and $C_H 3$ exon exchanged genes.

To add the αtp at the end of $C_\gamma 3$ of IgG2, a 346 base pair PCR fragment was generated using the primers 5'-CCGCTGCGCGGGTAAACCCACCC-3' (SEQ ID NO: 1) and 5'-CTGGATCCCCCCCTCCTGCACC-3' (SEQ ID NO: 2) and a 1.8 kb genomic fragment containing the α1 in Bluescript as template. The 5' primer also included base changes shown by underlining to include a Fsp I site to aid in cloning. The BamHI—Fsp I fragment was cloned into K2 with μ tail piece in pBR322 (Smith et al., 1995, J. Immunol. 154:2226–2236).

Expression of IgA1/IgG2 Hybrid Genes as Chimeric Antibodies in Sp2/0 Cells

Sal I-Bam HI fragments containing the constant region genes were cloned into the pSV2-Hgpt expression vector containing a murine $V_H$ region to produce antibodies specific for the hapten dansyl. The H chain expression vector was transfected into Sp2/0 cells expressing the dansyl specific chimeric kappa light chain gene by electroporation (Shin and Morrison, 1989, Methods Enzymol. 178:459–476).

About 8×10⁶ cells were washed in cold serum free IMDM and resuspended in 0.9 ml of the same medium and incubated on ice for 10 min with 10 μg of DNA in 0.1 ml of cold IMDM. Cells were pulsed with an electric field of 200 V and 960 μF in a Gene Pulser apparatus (Bio-Rad Laboratories, Richmond, Calif.). Cells were washed once and resuspended in 50 ml of IMDM containing 10% FCS. 100 μg/ml of mycophenolic acid was added to the wells to select for mycophenolic acid resistant colonies. After two weeks, the surviving colonies were screened for IgA production by ELISA as described below. Clones producing the highest quantities of IgA were expanded in IMDM containing 10% (v/v) BCS. All clones selected expressed more than 1 μg/10⁶cells/24 hours.

Co-expression of Chimeric Antibodies and Secretory Component in Sp2/0 Cells

Transfectants producing the domain exchanged antibodies were transfected with SC gene as described above. Cells were selected in medium containing 5 mM histidinol. Colonies secreting SC were detected using anti-SC ELISA.

Elisa

The levels of antigen specific IgA in culture supernatants were determined by ELISA as described previously (Chintalacharuvu et al., 1994, J. Immunol., 152:5299–5304). Briefly, microtiter plates were incubated overnight at 4° C. with 50 μl of supernatants from the 96-well plates containing transfectants. Bound IgA was detected by alkaline phosphatase-conjugated goat antiserum to human P L chain (Sigma Immuno Chem., St. Louis, Mo.). Color was developed by adding p-nitrophenyl phosphate (Sigma Chem. Co., St. Louis, Mo.) and the absorbance at 410 nM was determined in a microplate reader (MR 700 Dynatech, Chentilly, Va).

To detect transfectants secreting SC, microtiter plates were coated with guinea pig anti-SC diluted 1:4000 (v/v) in $Na_2CO_3$ buffer, pH 9.6. Antibody bound SC was detected by incubation with rabbit antiserum to human SC (Chintalacharuvu et al., 1991, J. Cell. Physiol., 148:35–47) diluted 1:2000 (v/v) in PBS containing 1% BSA (PBS-1% BSA) and 1% (v/v) normal guinea pig serum. Bound rabbit antibody was detected by incubating with alkaline phosphatase conjugated goat anti-rabbit IgG (Sigma Imm. Chem.) diluted 1:10,000 in PBS-1% BSA. Color was developed and detected as described above.

To detect antibody bound SC, microtiter plates coated with DNA-BSA were incubated overnight at 4° C. with 50 μl of supernatants from the 96-well plates containing transfectants. Antibody bound SC was detected by incubation with rabbit antiserum to human SC (Chintalacharuvu et al., 1991, J. Cell. Physiol., 148:35–47) diluted 1:2000 (v/v) in PBS containing 1% BSA (PBS-1% BSA). Bound rabbit antibody was detected by incubating with alkaline phosphatase conjugated goat anti-rabbit IgG (Sigma Imm. Chem.) diluted 1:10,000 in PBS-1% BSA. Color was developed and detected as described above.

Biosynthetic Labeling, Immunoprecipitation and SDS-PAGE Analysis

Transfectomas were biosynthetically labeled with [³⁵S]-methionine as previously described (Chintalacharuvu and Morrison, 1996, J. Immunol. 157:3443–49). Briefly, 1×10⁶ cells were washed twice and incubated at 37° C. for 30 min in methionine free medium. Cells were then incubated for 12 hours with 0.5 ml of methionine free medium containing 1% (v/v) FCS and 12.5 TCi of [³⁵S]-methionine. To immunoprecipitate secreted IgA, supernatants were incubated for 1 hour at 4° C. with 30 μl of 50% (v/v) dansylated-BSA coupled to Sepharose beads (DNS-BSA Sepharose). Antibodies bound to Sepharose beads were pelleted by centrifuging at 13,000×g for 2 min and washed twice with 1 ml of phosphate buffer, pH 7.8 containing 0.45 M NaCl followed by twice with 1 ml of PBS. Antibodies were eluted by incubating the beads for 10 min on ice in 30 μl of 3 mM Nε-Dansyl-L-Lysine (Sigma Chem. Co., St. Louis, Mo.) in phosphate buffer, pH 7.8 containing 0.45 M NaCl. The supernatants were analyzed by SDS-PAGE in phosphate-buffered 5% polyacrylamide gels and Tris-Glycine buffered 3.5% polyacrylamide gels under non-reducing conditions (Chintalacharuvu and Morrison, 1996, supra). For analysis under reducing conditions, samples were incubated at 37° for 1 hour in presence of 0.15 M2-mercaptoethanol and the proteins were separated in Tris-Glycine buffered 12.5% polyacrylamide gels.

Results

Generation and Expression of α1/γ2 Exon Exchanged Genes

Figure 2:
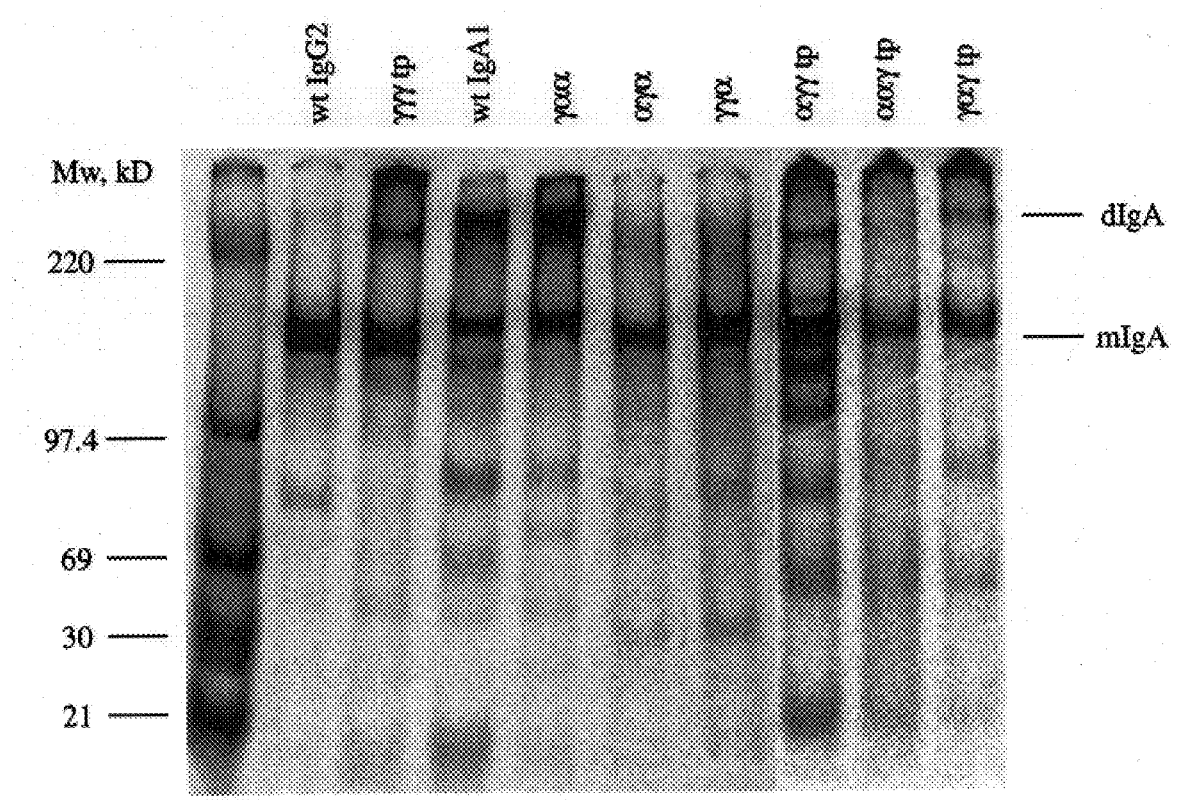
FIG. 2 shows the results of SDS-PAGE analysis of wild type IgA1, IgG2 and IgG2 and the domain exchanged proteins with the αtp secreted by Sp2/0 cells. Transfectants were biosynthetically labeled with $^{35}$S-methionine for 16 hrs. Labeled IgA proteins were precipitated from the culture supernatants with dansylated-BSA coupled to Sepharose and the proteins were analyzed by SDS-PAGE in 5% phosphate gels under non-reducing conditions. The position of the radiolabeled protein was determined using the relative mobility of molecular weight markers obtained from Amersham. MW: Molecular weight markers of 200, 94, 67, 43, 30 and 14.4 kD.

With the hinge and $C_H2$ considered as a single unit, the six possible combinations of α1/γ2 exon exchanged hybrid genes were generated (FIG. 1B, constructs 1–6). In addition, the 18 amino acid tail piece of a (αtp) was added at the carboxyl terminus of $C_H3$ of wild type γ2 and the hybrid genes containing the $C_H3$ of γ2 (FIG. 1B, constructs 7–10). The wild type and exon exchanged heavy chain genes were expressed in Sp2/0 myeloma cells previously transfected with the dansyl specific chimeric κ L chain. Transfectants synthesizing and secreting dansyl specific antibodies were initially identified by ELISA using antigen coated microtiter plates and with anti-hu κ used for detection. Monoclonal antibodies specific for the different domains of IgG2 were used to confirm that the heavy chains were of the correct structure (FIG. 1B). The cell lines were biosynthetically labeled by overnight growth in [³⁵S]methionine, and the Igs precipitated from the secretions with DNS-BSA-Sepharose and analyzed in 12.5% Tris-Glycine buffered gels under reducing conditions. All had H and L chains of the expected molecular weight. At least 5 independent clones from each of at least 2 transfections for each construct were analyzed to determine the assembly patterns of the domain exchanged antibodies. Representative clones analyzed by SDS-PAGE on 5% phosphate gels are shown in FIG. 2. All antibodies with Cγ3 (FIG. 1B, IgG2 and constructs 4–6) were produced only as monomers. In contrast, antibodies having Cα3 and Cγ3 with the αtp (FIG. 1B, constructs 1–3 & 7–10) were produced as both monomers and polymers, although the degree and extent of polymerization varied.

Figure 3:
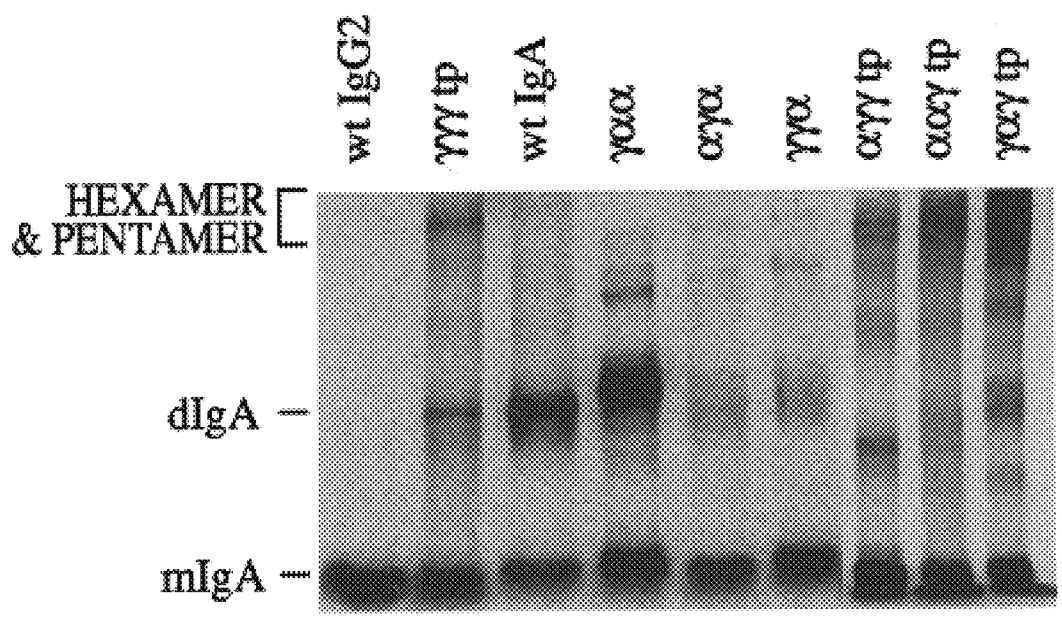
FIG. 3 shows the results of SDS-PAGE analysis of wild type IgA1, IgG2 and IgG2 and the domain exchanged proteins with the αtp secreted by Sp2/0 cells. Proteins were labeled as described in FIG. 2. Proteins were analyzed by SDS-PAGE in 3.5% Tris-glycine gels under nonreducing conditions.

The Igs that formed polymers were further analyzed on 3.5% Tris-glycine gels which can more effectively resolve the higher polymeric forms (FIG. 3). Densitometric analysis of the bands was used to determine the relative amounts of the monomers and polymers (Table 1). As has been previously observed, wild type IgG2 showed a single band of Mr 170 kD corresponding to monomer and wild type IgA1 showed two predominant bands with Mr 180 and 350 kD corresponding to IgA monomer and dimer. Presence of the α tail piece at the end of $C_H3$ resulted in the presence of higher order polymers migrating at the position of pentameric and hexameric IgM. For IgG2 with the α tail piece, 51% of the radioactivity appeared as a band with a Mr of 320 kD corresponding to dimer and about 20% of the radioactivity appeared as band with a Mr~10⁶ kD corresponding to pentamer/hexamer (FIG. 3 & Table 1). In contrast, higher order polymers were not formed when αtp was positioned at the end of Cα3. A small amount of αγα (20%, Table 1) and γγα (15%, Table 1) were present as dimer while the remainder was monomers. When Cα3 was joined to Cα2, efficient dimer formation equivalent to that of the wild type IgA1 was observed. These results suggest that both $C_H2$ and $C_H3$ of IgA are important for efficient dimer formation and that $C\alpha3$ prevents the formation of higher polymers.

When αγγtp was analyzed, 41% of the radioactivity was observed as a band corresponding to monomer, 28% as dimer and 25% as pentamer/hexamers with about 7% of the radioactivity observed as intermediate polymers. Although, 45% of αγγtp and 40% of γαγtp was observed as monomer and 45% of αγγtp and 32% of γαγtp was observed as pentamer/hexamers with only 5% of αγγtp and 10% of γαγtp present as dimers. In addition, 19% of γαγtp was also found as intermediate polymers. These results suggest that the presence of the αtp at the end of $C_H3$ of IgG2 enables wild type IgG2 and hybrid molecules with $C_H3$ of IgG2 to form higher order polymers. Only when the $C_H2$ of IgA is present, is there efficient formation of predominately dimers.

Role of $C_H3$ of IgA in Incorporation of J Chain

Figure 4:
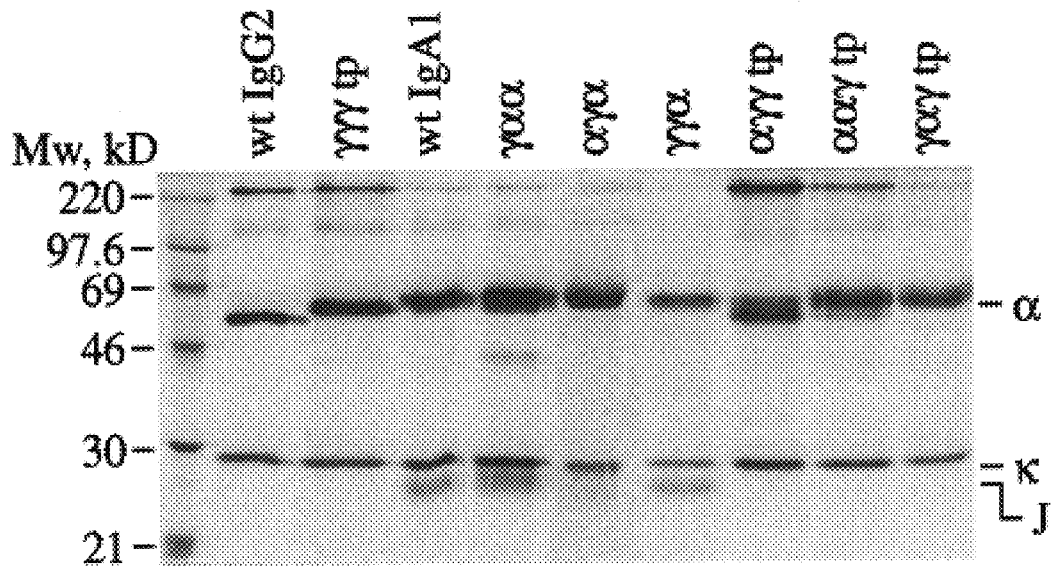
FIG. 4 shows the results of SDS-PAGE analysis of wild type IgA1, IgG2 and the domain exchanged proteins with αtp secreted by Sp2/0 cells. Proteins were labeled as described in FIG. 2. Proteins were analyzed by SDS-PAGE in 3.5% Tris-glycine under reducing conditions. The position of the radiolabeled protein was determined using the relative mobility of molecular weight markers obtained from Amersham. MW: Molecular weight markers of 200, 94, 67, 43, 30 and 14.4 kD.

To determine if the polymeric Igs incorporated J chain, γαα, αγα, γγα, αγγtp, ααγtp, γαγtp were analyzed by SDS-PAGE under reducing conditions in 12.5% Trisglycine gels (FIG. 4). When wild type IgA and γαα, αγα, γγα were analyzed, bands corresponding to H, L and J chain were observed. In contrast, when wild type IgG2, αγγtp, ααγtp, γαγtp were analyzed, bands corresponding to H and L chains but not to J chain were observed. These results suggest that in addition to the αtp, the presence of structure (s) in the $C_H3$ of IgA are important for covalent incorporation of J chain into polymers.

The Role of α Domains and J Chain in Binding to SC

To determine the role of the a constant domains and J chain in binding to SC, transfectants secreting either the wild type IgA or the domain exchanged proteins were transfected with the gene for SC as described by Chintalacharuvu and Morrison (Proc. Natl. Acad. Sci., USA, 1997, 94:6364–6368). Stable SC transfectants were identified by ELISA using guinea pig anti-SC to capture bound and/or free SC, and rabbit anti-SC as the detecting antibody. Positive colonies were expanded. SC bound to antibody was detected by screening the supernatants by a second ELISA using antigen-coated microtiter plates to capture the antibody and rabbit anti-SC as the detecting antibody. SC was bound to wild type IgA and γαα, αγα and γαα proteins, whereas it was not bound to wild type IgG2, IgG2 with the αtp and αγγtp, ααγtp and γαγtp proteins. These results suggest that in addition to αtp, structure(s) in $C_H3$ of IgA are required for binding to SC. Since IgG2 with the αtp and αγγtp, ααγtp and γαγtp do not contain J chain (FIG. 4), it is possible that J chain is essential for binding of polymers to SC.

Discussion

Secretory IgA (and IgM) is unusual among Igs in that it contains 4 different polypeptide chains, the H, L, and J chains and SC. Sequence alignment shows that the α H chain (and μ H chain) contains an additional 18 amino acids (tail piece) at the carboxyl terminus of $C_\alpha3$ or $C_\mu4$ (D. Beale and A. Feinstein, 1976, Quart. Rev. Biophys., 9:135–180). The results presented herein show that the α tail piece is sufficient to form polymers in the context of $C_H3$ from IgG2. However, the presence of αtp is not sufficient for the incorporation of J chain. Through the use of a family of IgA1/IgG2 domain exchanged proteins, this Example shows that $C_\alpha3$ is required for incorporation of J chain into polymers, suggesting that initial interactions between the $C_\alpha3$ and J chain are required before a covalent bond can form between the penultimate Cys of α H chain and J chain. Structural analysis suggests that J chain consists of one or two domains with Ig domain-like folding of its polypeptide (G. Cann et al., 1982, Proc. Natl. Acad. Sci., USA, 79:6656–6660; J. Zikan et al., 1985, Proc. Natl. Acad. Sci., USA, 82:5905–5909). Noncovalent interactions between $C_\alpha3$ and domain structures in J chain may be a prerequisite for disulfide bonding with the α H chains.

In contrast to proteins containing Cα3, proteins containing Cγ3 and the α tail piece did not bind J chain and preferentially formed polymers larger than dimers. The presence of J chain may be responsible for restricting the polymerization of dimers in IgA-producing cells. In IgM producing cell lines, the presence of J chain leads to the production of pentamers and the absence of J chain leads to the secretion of hexamers (M. J. Niles, et al., 1995, Proc. Natl. Acad. Sci., USA, 92:2884–2888).

Although $C_H3$ of IgA was sufficient to form dimers, both $C_H2$ and $C_H3$ of IgA were required to form dimers efficiently. This result suggests that sequences in $C_H2$ of IgA may also contribute to the assembly of dimers.

Example 2

Role of IgA Tail Piece and IgM Tail Piece in Polymerization and Association with J Chain Both IgM and IgA possess an 18 amino acid extension of the C terminus (tail-piece, tp) that participates in polymerization through a penultimate cysteine residue. Although of identical length, the sequence of the IgA tail piece (αtp) and the IgM tail piece (μtp) differs as shown in Table 1. In this example, the effects of these sequence differences on the polymerization and association with J chain are assessed by placing the μtp in the context of the IgA1 constant region and the αtp in the context of IgG2 and IgM constant regions.

Although both αtp and μtp give rise to polymers in these contexts, IgAμtp, and IgMαtp are deficient in their ability to incorporate J chain as compared to their wild-type counterparts. IgG2 with a αtp or μtp form polymers but do not incorporate J chain. The degree of polymerization depends on the associated constant region indicating that the tailpiece by itself does not contain the information responsible for the extent of polymerization, namely dimers in the case of IgA and pentamers/hexamers in the case of IgM. Therefore, additional structural determinants in the constant region of a particular isotype must also contribute to determining the type of polymers formed.

Construction of an IgG Containing the Alpha Tail-piece

The αtp from IgA1 was modified with restriction sites for cloning using PCR. A 5' primer CCGC TGCGCAGGTAAACCCACCC (SEQ ID NO: 3) introduced a Fsp I blunt site (underlined) at the end of $C_H3$ of IgA and the 3' primer CTGGATCCCCCCCTCCTGCACC (SEQ ID NO: 4) contains a BamH I site and anneals in the intron downstream of the αtp. The Fsp I/BamH I PCR fragment was used to replace the μtp in plasmid pBR4644, which contains γ2μtp. From the resulting plasmid pBR1724, the γ2αtp was removed and cloned into the DNS heavy chain expression vector, generating pAG1725.

Construction of an IgM Containing the Alpha Tail-piece

An NgoM I site was introduced just upstream of the αtp by PCR overlap mutagenesis resulting in a silent mutation. In a first PCR reaction, the oligonucleotide with the sequence CACAGCCCCGGGGTGCCCACCA (SEQ ID NO: 5) (Sma I site underlined), which annealed within the constant region of an IgA gene in plasmid pBS5202, was used as the 5' primer together with a 3' anti-sense mutagenic oligo GGTGGGTTTGCCGGCCAAGCGGT (SEQ ID NO: 6), which includes two nucleotide changes (bold) to introduce a NgoM I site. A parallel reaction was performed with a 5' oligo complementary to the mutagenic primer and a 3' primer AACTAGTGGATCCCCCCCTCCT (SEQ ID NO:

7) (with a BamH I site) annealing in the intron downstream of the αtp gene. The overlapping PCR was carried out with the external primers (5'Sma I and 3'BamH I). After sequencing, the Sma I-BamH I fragment was cloned in a pUC plasmid generating pUC6404. To join the αtp on to the m heavy chain, the AgeI-BamHI piece from m was replaced with the NgoM I-BamH I αtp fragment producing plasmid pBS6416. The Sal I-Bam H I cassette including the m constant region with the αtp was then used to produce the DNS heavy chain expression vector pAG6406.

Construction of an IgA Containing the m Tail-piece

The μtp was joined to the end of the $C_H3$ of IgA by a Sca I to NgoM I/Age I to BamHI triple ligation in plasmid pUC4605. The EcoR I-Kpn I fragment from this clone, which contains a portion of the IgA $C_H3$ with the μtp, was moved into pBS4213, a subcloning plasmid which lacks a Sma I site resulting in pBS6407. The Sma I-BamH I cassette from this plasmid was replaced by a wild type IgA constant region creating pBS6417. Finally, the BamH I-Sal I fragment containing the complete IgA constant region fused to the μtp was cloned in the DNS heavy chain expression vector.

Production and Analysis of Recombinant Proteins

The γ-μtp, γ-αtp, μ-αtp and α-μtp heavy chain expression vectors were transfected into the TWS cell line. TWS is a derivative of the non-immunoglobulin producing mouse myeloma cell line Sp2/0 which secretes a transfected chimeric anti-DNS Vk-human Ck light chain (Dangl, J. L. et al., 1988, Embo Journal 7(7):1989–94). Transfectants were selected with mycophenolic acid (3 mg/ml) and provided with hypoxanthine (125 mg/ml) and xanthine (7.5 mg/ml). Surviving clones were screened for antibody production by ELISA using DNS-BSA coated microtiter plates and anti-human IgG, IgM or IgA Fc alkaline phosphatase conjugated polyclonal goat antibody (Sigma Chemical Co., St. Louis, Mo.). Positive clones were expanded and maintained in Iscove's modified Dulbecco's medium (IMDM) containing 5% calf serum.

The antibodies were analyzed by metabolic labelling and immunoprecipitation. Between 3 and $5 \times 10^6$ cells were washed and resuspended in 1 ml labeling medium (high glucose DME deficient in methionine: GIBCO/BRL, Grand Island, N.Y.) containing 25 mCi $^{35}$S-Methionine (Amersham Corp., Arlington Hts., Ill.) and allowed to incorporate label for 3–4 hours or overnight with the addition of 1% FCS or aCS at 37° C. under tissue culture conditions. After labeling, the antibodies were immunoprecipitated with 2.5 ml of a rabbit anti-human IgG, IgM or IgA Fc and anti-human Fab polyclonal antiserum and a 10% suspension of S. aureus with membrane bound Protein A (IgGSorb, Enzyme Center, Woburn, Mass.). The precipitated labeled antibody was then resuspended in 50 ml loading buffer (25 mM Tris, pH 6.7, 0.2% SDS, 10% glycerol, ~8 mg/100 ml bromphenol blue), boiled for 2 minutes, and analyzed by SDS-PAGE (4% tris-glycine buffered SDS polyacrylamide gels for polymeric Abs or 5% sodium phosphate buffered polyacrylamide gels for monomeric Abs and IgA). To examine heavy and light chains separately, a portion of the labeled sample was reduced by treatment with 0.15 M b-mercaptoethanol at 37° C. for 30 min and analyzed on 12.5% Tris-glycine buffered polyacrylamide gels.

Chimeric antibodies were purified from culture supernatant by DNS-Sepharose affinity chromatography as described previously (Tao, M. H., and Morrison, S. L., 1989, J. Immunol. 143(8):2595–601) and the concentration determined by a BCA Protein Assay (Pierce, Rockford, Ill.). Purified antibodies were then analyzed by SDS-PAGE, unreduced on 4% tris-glycine gels and reduced on 12.5% tris-glycine gels.

Tunicamycin Treatment of Cells

Between 3 and $5 \times 10^6$ cells were washed 2 times with PBS and resuspended in 1 ml of medium with 5% aCS and pretreated with 8 mg/ml of tunicamycin (Boehringer-Mannheim, Indianapolis, Ind.) for 4–5 hours. Then the cells were metabolically labeled as described above in 1 ml of labeling medium containing 25 mCi $^{35}$S-Methionine and 8 μg/ml of tunicamycin.

J Chain Detection

An anti-J chain immunoblot was performed by separating affinity purified antibody on a 12.5% tris-glycine gel under reducing conditions and transferring to Bioblot-NC nitrocellulose (Costar, Cambridge, Mass.) according to the method of Towbin et. al (1992, Biotechnology 24:145–9). Non-specific sites were blocked by incubating the blot for 2 hrs at room temperature in PBS containing 0.1% (v/v) Tween-20 and 5% (w/v) dried milk and probing first with rabbit anti-J chain (Nordic Immunology, Capistrano Beach, Calif.) and then with $^{125}$I-labeled goat-anti-rabbit IgG (ICN Radiochemicals, Irvine, Calif.). Alternatively, antibody concentrated from cell culture media by incubating 10 ml of supernatant with 100 μl of DNS BSA-coated sepharose beads and eluted with 60 μl of 3 mM DNS-lysine (Sigma Chemical Co.) was resuspended in sample buffer, boiled, and subjected to SDS-PAGE as described above. A rabbit anti-J chain or rabbit anti-kappa (Sigma Chemical Co.) was used as primary antibody. A donkey anti-rabbit-HRP conjugated was then used and detected using the ECL system (PIERCE, supersignal substrate) as recommended by the manufacturer. Additionally, the presence of J chain was observed in a 12.5% tris-glycine gel as a band migrating with an apparent molecular weight of 20–23 kDa.

Results

Although similar, the tail-pieces of IgM (μtp) and IgA (αtp) differ at seven of 18 positions (Table 1). Polymeric IgA is present mainly as dimers, while polymeric IgM is pentameric and hexameric. To investigate the contribution of the tail-piece to the polymerization state of an antibody, the tail-piece of IgM or IgA was added to different Ig H chain isotypes.

TABLE 1

Comparison between $α^+$ and μ tail-pieces

/ / / / / / / / / / * * / / / * / / * * * *

μtp: GK/<u>PTLYNVSLVMSDTAGTCY</u>

αtp: K/<u>PTHVNVSVVMAEVDGTCY</u>

Figure 5:
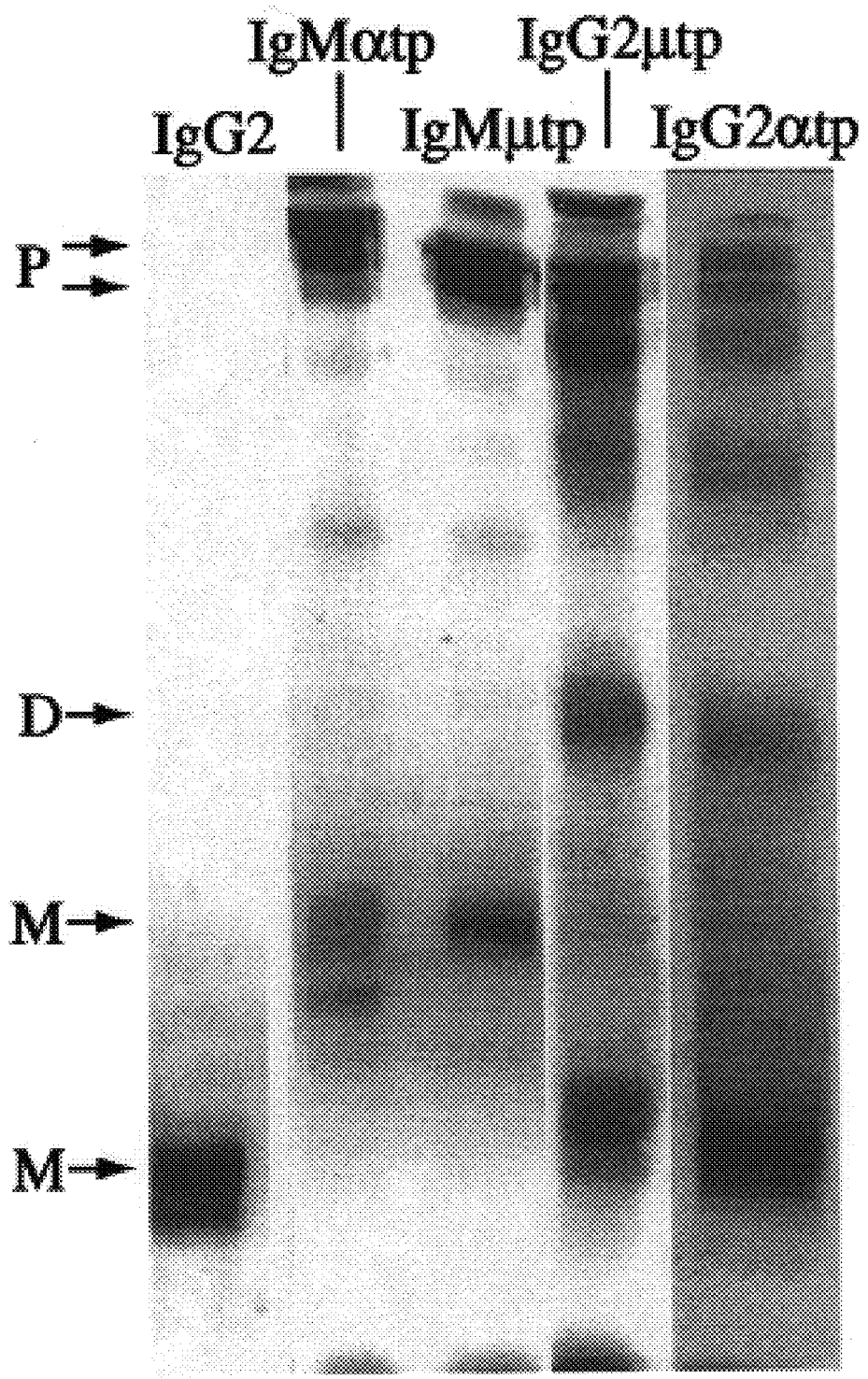
FIG. 5 is a gel showing that IgG2αtp and IgG2μtp as well as IgMαtp and IgMμtp display similar polymerization patterns. IgGαtp, IgG2μtp, IgMαtp and IgMμtp were biosynthetically labeled by overnight growth in medium containing [$^{35}$S] methionine. Secretions were prepared and immunoprecipitated using rabbit anti-human Fc+Fab and IgGSorb. The immunoprecipitates were analyzed on 4% tris-glycine SDS gels in the absence of reducing agents. IgG2 is included to mark the position of the $H_2L_2$ monomer form. The position of different polymeric forms is indicated by arrows: M=monomers, D=dimers, P=polymers.
Figure 6A:
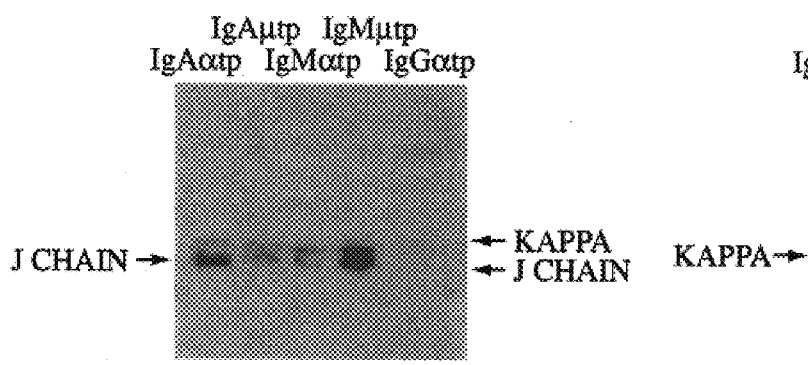
FIG. 6A is a Western blot showing J chain incorporation by polymers of IgA αtp, IgAμtp, IgM μtp, IgM αtp and IgG αtp. Supernatants were concentrated by incubating them with DNS-BSA-sepharose and then eluting with DNS-lysine. The protein concentrates were separated on 12.5% tris glycine gels and a Western blot performed. The membranes were probed with anti-J chain.
Figure 6B:
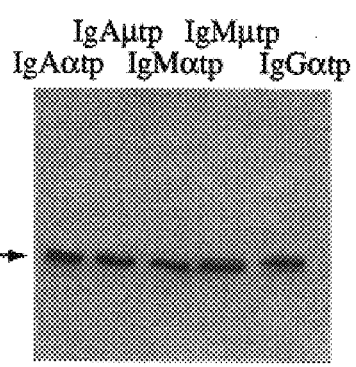
FIG. 6B is a Western blot prepared as in FIG. 6A, except that the membranes were probed with anti-kappa.
Figure 6C:
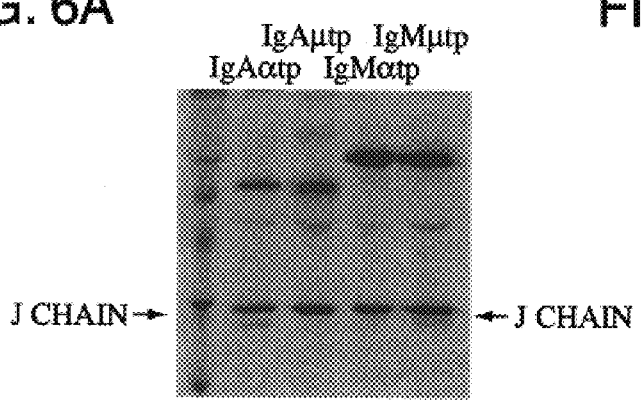
FIG. 6C is a gel showing the protein concentrates prepared as in FIG. 6A and shows immunoprecipitates of overnight biosynthetic labels separated on 12.5% tris glycine gels.

*Amino acid differences
+IgA2(μ2) has an I at position four
N = Asn at which N-linked carbohydrate is attached
C = the penultimate cysteine important for polymerization The assembly state of secreted IgMαtp resembles wild type IgM (IgMμtp) produced in the same cell system. In both cases, predominately fully assembled polymers corresponding to pentamers/hexamers are secreted although there is some secretion of lower molecular weight forms, mainly monomers (FIG. 5). However, the possibility cannot be excluded that the monomers were from cells that lysed during the course of the overnight label. IgG2αtp and IgG2μtp were assembled as polymers ranging from dimers to pentamers/hexamers but monomers were also detected (FIG. 5). Although J chain was present in both IgMμtp and IgMαtp, the amount present appears to be decreased in the latter when equivalent amounts of protein were analyzed by Western blot (FIG. 6A). Furthermore, J chain was below the level of detection when radiolabeled secreted IgMαtp was analyzed (FIG. 6C). J chain was not found associated with the IgG2αtp polymers; in previous studies J chain had not been found associated with IgG polymers containing the μtp (FIG. 6A, C)(Smith, R. I. et al., 1995, J. Immunol. 154(5) :2226–36). Therefore the αtp and μtp appear to be equivalent in their ability to effect the oligomerization of IgG; however they are not equivalent in mediating J chain association with polymeric IgM.

Figure 7A:
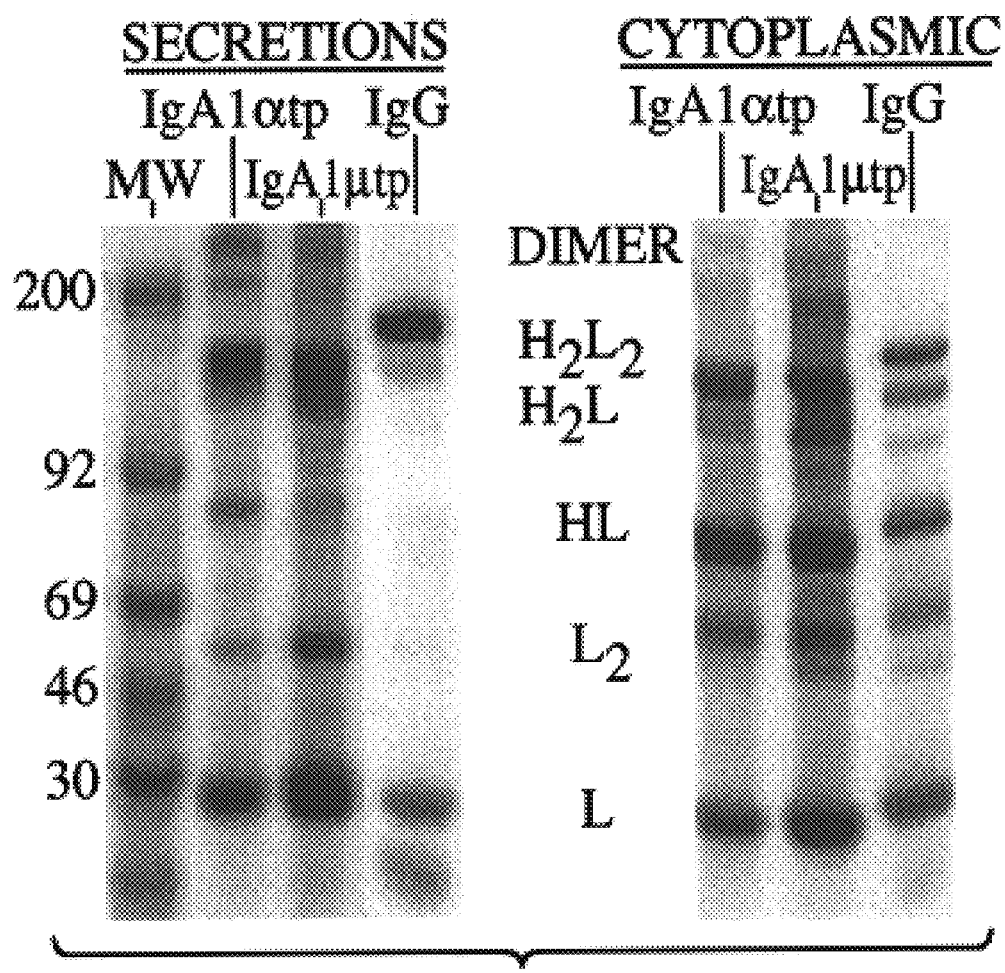
FIG. 7A shows assembly patterns of cytoplasmic and secreted IgA1αtp and IgA1μtp. IgA1αtp and IgA1αtp were biosynthetically labeled by overnight growth in medium containing [$^{35}$S] methionine. Cytoplasmic lysates and secretions were prepared and immunoprecipitated using rabbit anti-human Fc+Fab and IgGSorb. The immunoprecipitates were analyzed on 5% phosphate SDS gels in the absence of reducing agents. IgG3 is included to mark the position of the $H_2L_2$ monomer form. The position of the different assembly intermediates is indicated by arrows.

The αtp and μtp do not function equivalently in promoting the oligimerization of IgA. A larger proportion of IgA1μtp was secreted as monomers than IgA1αtp (FIG. 7A). To eliminate the possibility of clonal variation, independent transfectants were analyzed. Intracellularly, abundant half-molecules corresponding to the HL assembly intermediate typical of IgA1 are seen for both IgA1αtp and IgA1μtp; however IgA1μtp has a significant increase in the $H_2L$ assembly intermediate.

IgA1μtp is less efficient than IgA1αtp in incorporating J chain. Western blotting of equivalent amounts of DNS-affinity isolated antibodies show that J chain is in fact present in IgA1μtp albeit in decreased amounts when compared with wild type IgA1 (FIG. 6A). However, analysis of secreted radiolabeled immunoprecipitates in a reducing SDS-PAGE reveals no J chain in IgA1μtp in contrast to what is seen with wild type IgA1αtp polymers (FIG. 6C)(Atkin, J. D. et al., 1996, J. Immunol. 157(1), 156–9).

Figure 7B:
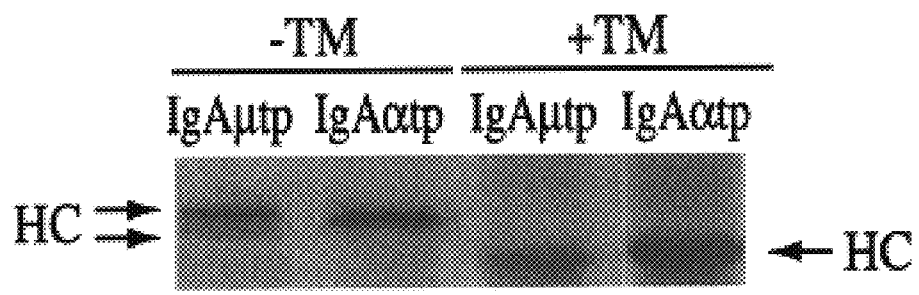
FIG. 7B is a gel showing that the IgA1μtp heavy chain is less gylcosylated than IgA1αtp. IgA1μtp and IgAαtp were biosynthetically labeled by overnight growth in medium containing [$^{35}$S] methionine in the presence and absence of tunycamycin (TM). Immunoprecipitated secretions were prepared and analyzed on 12% tris-glycine SDS gels in the presence of a reducing agent. HC=heavy chain.

The heavy chain of IgA1μtp is resolved as a doublet in reducing SDS-PAGE on 12% Tris glycine gels. This double band represents variation in the level of glycosylation as treatment of cells with tunicamycin during biosynthetic labeling yields IgA1μtp and IgA1αtp heavy chains of equivalent sizes (FIG. 7B). Therefore IgA1μtp also differs from IgA1αtp in its extent of glycosylation.

Discussion

In contrast to IgG, both IgA and IgM exist as polymeric Igs. However, IgA is secreted mainly as dimers, whereas IgM is secreted as pentamers and hexamers. An unresolved issue is what structural features are required for polymerization and what determines the degree of polymerization. Both IgA and IgM contain an 18 amino acid carboxy-terminal extension; although both the αtp and the μtp have a conserved penultimate cysteine and an N-linked glycosylation site, there are 7 amino acid differences between the two tail-pieces (Table 1). It is possible that these sequence differences might be responsible for the differences seen in the polymerization state and assembly of IgA and IgM.

In a previous study we demonstrated that the addition of the μtp to the carboxy terminus of IgG is sufficient for polymer production. However, monomeric IgGμtp was also secreted indicating that a non-polymerized μtp alone is an insufficient signal for intracellular retention, contrary to what has been previously suggested (Klausner, R. D., and Sitia, R., 1990, Cell 62(4):611–4).

In the present study we added the tail-piece from IgA1 to the carboxy terminus of IgG2. Both the penultimate Cys471 homologous to Cys575 in the μtp and the N-linked carbohydrate addition site at Asn459 have been reported to be necessary for the assembly of IgA dimers (Atkin, J. D. et al., 1996, J. Immunol. 157(1), 156–9). IgG2αtp was secreted in sizes ranging from monomers to hexamers. Therefore, in the context of an IgG antibody, μtp and αtp both cause the same degree of polymerization suggesting that the αtp itself does not contain the information responsible for the formation of dimers, the predominant polymeric form of IgA. In addition, as was observed with the IgGμtp polymers, IgG2αtp does not incorporate J chain. Thus polymerization of IgG with both tail-pieces is independent of this polypeptide. This is in contrast with what is observed with IgA1 in which J chain is necessary for the assembly of dimers (Brewer, J. W., and Corley, R. B., 1997, Mol. Immunol. 34(4):323–31; Fazel, S. et al., 1997, Internat'l Immunol. 9(8), 1149–58).

When the αtp was placed at the carboxy-terminus of IgM and the μtp was placed in the equivalent position of IgA1, polymerization was similar to that seen with the unmodified proteins. IgM with the αtp resembled wild type IgM, with the majority of the protein assembled into covalent pentamers/hexamers. In addition like wild type IgA1, IgA1μtp assembles dimeric, not petameric and hexameric polymers. Therefore the structure of the tail-piece is not sufficient to control the types of polymers formed. Additional structural determinants in the constant region of a particular isotype must also contribute to determining the type of polymers formed. However, changing the tail-pieces did affect the efficiency of incorporation of J chain into the polymers. Reduced levels of J chain were found in IgM αtp and IgAμtp compared to that present in IgMμtp and IgAαtp. In addition changing the tail-piece influenced the assembly of IgAμtp. Cytoplasmic immunoprecipitates from IgAμtp revealed abundant intracellular HL, an assembly intermediate typical of IgA1, and $H_2L$ which is unusual for this subclass of IgA where the major assembly pathway is H+L->HL->$H_2L_2$ (Chintalacharuvu, K. R. et al., 1994, Hepatology 19(1):162–73). Likewise, the presence of the μtp in IgA1 results in the secretion of two glycosylation variants of the heavy chain possibly due to partial glycosylation of the μtp addition site suggesting altered accessibility when it is in the context of IgA1.

Example 3

Role of Oligosaccharides in the Polymerization and Effector Functions of IgGμtp

In this Example, the role of oligosaccharides in the polymerization and effector functions of IgGμtp is assessed. IgG1μtp and IgG3μtp genes lacking the carbohydrate addition site in $C_H2$, in the tail-piece or completely devoid of carbohydrates were constructed. The resulting aglycosylated molecules were able to form polymers in contrast to previous reports (Wiersma, E. J. et al., 1997, J. Immunol. 158(4) :1719–26; Krugmann, S. et al., 1997, Biochem. Soc. Trans. 25(2):323S). Aglycosylated polymers retained the ability to activate complement as assayed by C1q binding and hemolysis, although they were not as effective as their wild type polymer counterparts. Although, IgGμtp lacking the carbohydrate in the tail-piece was able to bind to FcgRII, completely aglycosylated polymers lost their ability to bind to both FcgRI and FcgRII, suggesting a critical role for the $C_H2$ sugar in the FcR binding. Absence of the μtp carbohydrate increases the half life of polymeric IgG1, whereas absence of the carbohydrate in $C_H2$ accelerates the clearance rate.

Construction of Polymeric IgG Lacking Carbohydrate in CH2

Figure 8:
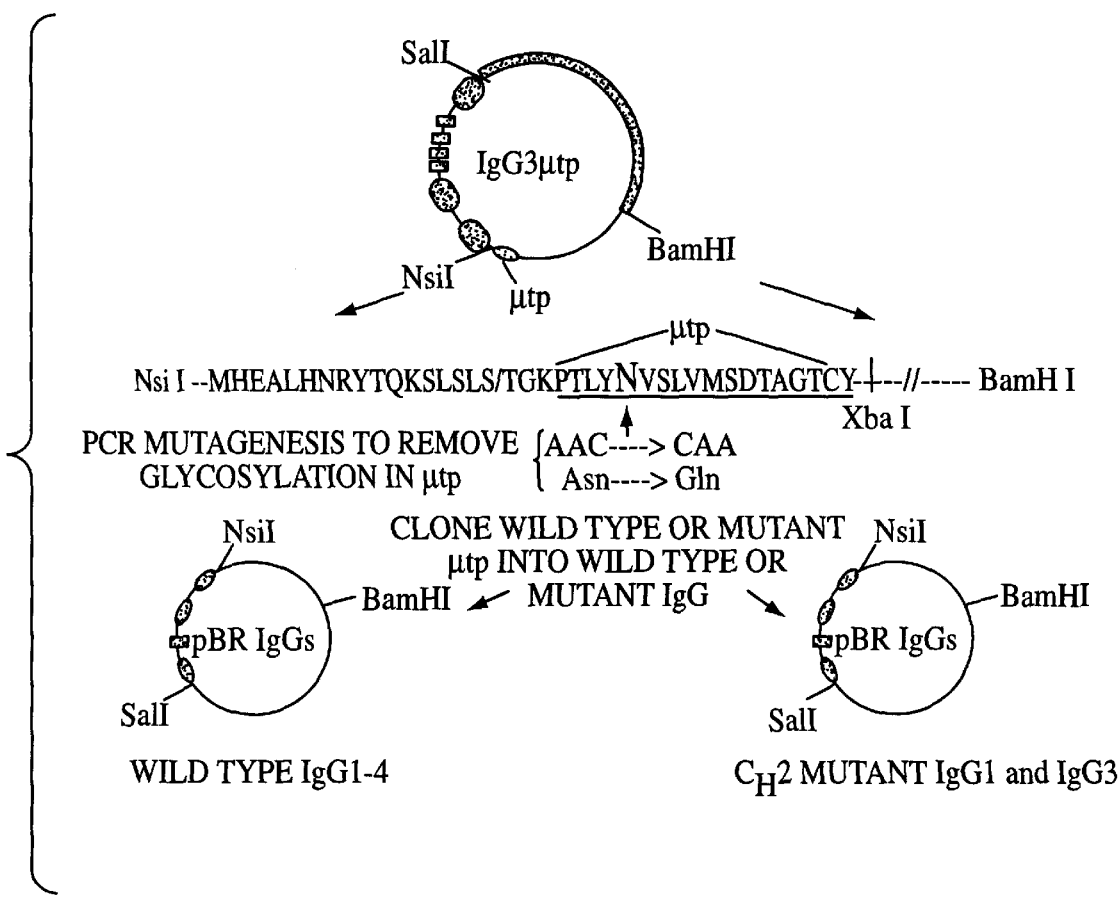
FIG. 8 depicts a general strategy for producing carbohydrate mutant polymeric IgGs. The μtp previously cloned into IgG3 was removed by a Nsi I-BamH I digest. The μtp sequence is underlined, and a (/) separates the three last amino acids of IgM that replace those of IgG as a result of the cloning. PCR mutagenesis was performed to remove the glycosylation addition site in the 5$^{th}$ amino acid in μtp (indicated by arrow). The wild type or mutant μtp was cloned 3' of wild type or aglycosylated IgGs as a Nsi I-BamH I fragment. The constant region-μtp fusions were then transferred as Sal I-BamH I fragments to a heavy chain expression vector.

The μtp coding sequence was originally transferred from pNCmTNP to the IgG3 gene by ligation at engineered Sca I restriction sites (Smith, R. I., and Morrison, S. L., 1994, Biotechnology N Y 12(7):683–8). To transfer the μtp to the γ constant regions we used an Nsi I restriction site conserved in the $C_H3$ of all four γ genes previously cloned as Sal I-BamH I fragments in pBR plasmids. The N-linked glycosylation addition site in the $C_H2$ of human IgG1 and IgG3 had been previously removed by site directed mutagenesis by changing Asn297 (AAC) to Gln(CAG). pSV4661 and pSV4662 are expression vectors that contain these mutant constant regions as Sal I-BamH I fragments. To attach the 18 amino acid μtp (FIG. 8), we cloned the Sal I-Nsi I fragment of the mutant constant regions into plasmid pBR4644 which contains a wild type IgG2 constant region followed by the μtp. The resulting plasmids pBR4663 (IgG1) and pBR4664 (IgG3) were then cut with Sal I-BamH I and the entire constant region cloned into an expression vector (Tan, L. et al., 1985, J. Immunol. 135(5):3564–7) containing an anti-DNS $V_H$. The expression vectors generated are pAG4665 and pAG4666 and to illustrate their lack of carbohydrate (Cho) in $C_H2$, they were named IgGμtpΔChoC$_H$2.

Generation of a Mutant μ Tail Piece Lacking the Carbohydrate Addition Site

The μtp has an N-linked carbohydrate addition site at its fifth amino acid. To remove it, PCR mutagenesis was performed using a long (97 mer) 5' mutagenic primer which encompasses the Nsi I cloning site, removes a Sca I site at the end of $C_H3$, and replaces the Asn in the μtp with Gln. A 3' primer complementary to an intronic sequence 350 bp downstream of the μtp where a unique Xba I site is located was used for amplification. PCR was performed using 100 ng of pBR4644 ($_{γ2}$μtp) as template. The resulting 400 bp product was cloned into a TA vector (Invitrogen) resulting in plasmid pCR4956 and was sequenced.

Construction of Completely Aglycosylated Polymeric IgG Genes

To construct completely aglycosylated polymeric IgG1 and IgG3 lacking both carbohydrates in the $C_H2$ and the μtp, the μtp lacking carbohydrate from pCR4956 was used to replace the wild type μtp in plasmids pBR4663 and pBR4664, respectively by cloning it as a Xba I-Nsi I insert. The absence of the Sca I site in $C_H3$ confirmed the presence of the correct insert. The plasmids generated, pBR4958 and pBR4959, were cut with Sal I and BamH I, and the 5 Kb and 5.6 Kb inserts were cloned into pAG4882 to produce the expression vectors pAG4962 (IgG1) and pAG4961 (IgG3). These were designated IgGμtpAglyc to indicate the complete lack of sugar.

Construction of Polymeric IgG Without Carbohydrate in the μtp

To obtain polymeric IgGs with a single carbohydrate in the $C_H2$, but lacking the μtp sugar, different strategies were followed for each isotype. For IgG1, the mutant μtp from PCR4956 was used to replace the wild type μtp in pBR4642, by inserting it as a Nsi I—Xba I fragment, generating pBR4955. This plasmid was then cut with Sal I and BamH I and the constant region-μtp fusion moved to pAG4882 to produce the expression vector pAG4960.

The IgG3 expression vector was made by replacing the constant region of pBR4955 (IgG1μtpΔChoC$_H$2) with a wild type IgG3 constant region as a Sal I-Nsi I fragment. The resulting plasmid pBR4963 was then cut with Sal I and BamH I and the fragment containing the constant region-μtp gene cloned into pAG4882, generating the expression vector pAG4964. The lack of carbohydrate (Cho) in the μtp was designated IgGμtpΔChoμtp.

Endoglycosidase H Treatment

To analyze the state of processing of the glycans in the polymerized IgG mutants, labeled immunoprecipitated antibody bound to StaphA-sepharose was resuspended in 100 ml of reaction buffer (0.1M citrate containing 1 ml b-mercaptoethanol and 1 ml of 250 mM PMSF), and 10 ml of Endoglycosidase H added (Boehringer Manheim). The digestion was allowed to proceed for 18 to 24 hours at 37° C. After boiling for 2 min the antibodies were analyzed by PAGE under reducing conditions in a 12.5% tris-glycine gel.

C1q Binding

An ELISA type assay to detect C1q binding was used as described (Smith, R. I., and Morrison, S. L., 1994, Biotechnology N Y 12(7):683–8). 100 ml/well of the antibodies diluted in 1% BSA at concentrations ranging from 0 to 20 mg/ml were incubated in DNS-BSA (40:1 substitution) coated plates and blocked with 3% BSA at room temperature for 2 hours. After washing with HBS plus 0.02% sodium azide, normal human serum (NHS) diluted to 0.125% in HBS was applied in a volume of 100 ml at 37° C. for 2 hours. 1:10,000 diluted goat anti-human C1q (Atlantic Antibodies, Stillwater, Minn.) was allowed to bind to C1q and then a 1:20,000 diluted swine anti-goat IgG-alkaline phosphatase conjugate (Boehringer Manheim) was used to detect the bound goat IgG. 100 ml p-nitrophenyl phosphate (Sigma Chemical Co.) at 0.6 mg/ml in 9.6% diethanolamine, 0.24 mM $MgCl_2$, pH 9.8, was added as a phosphatase substrate and the optical density read at 410 nm.

Complement-mediated Hemolysis

The assays were performed as described (Smith, R. I., and Morrison, S. L., 1994, Biotechnology N Y 12(7):683–8). Dilutions of recombinant antibodies in Gel-HBS (0.01M Hepes, 150 mM NaCl, 0.15 mM $CaCl_2$, 0.5 mM $MgCl_2$, 0.1% gelatin, pH 7.4) were added to round bottom 96-well plates (Coming Glass Works, Corning, N.Y.) in a volume of 50 ml. Then 50 ml of 2% sheep red blood cells (SRBC) loaded with $^{51}Cr$ and coated with DNS-BSA and 25 ml undiluted normal human serum (NHS) preabsorbed against DNS-BSA coated cells were added. The plates were incubated at 37° C. for 45 min, unlysed SRBC were pelleted by centrifugation and 50 μl of supernatant counted in a gamma counter. Each point was assayed in triplicate and the percent lysis was calculated.

FcgR Binding

The multipotential hematopoietic cell line K562 was used to study binding to the low affinity receptor, FcgRII. 5–8× $10^8$ unstimulated K562 cells were washed twice with cold PBS and incubated in DMEM without serum for two hours at 37° C., 5% $CO_2$ prior to the assay. The cells were resuspended in binding buffer (0.1 M Hepes free acid, 0.12 M NaCl, 5 mM KCl, 1.2 mM $MgSO_4$, 15 mM HAc, 10 mM glucose, 1% BSA, pH 7.4–7.7) and $2×10^6$ cells incubated with $10^5$ cpm $^{125}$I-labeled antibody in the presence of various amounts (0–500 fold excess) of unlabeled competitor antibody in duplicate. The assay was performed with rotation at 15° C. for 3 hours in 0.25 ml binding buffer. The suspension of cells was then layered over 200 ml binding oil (84:16, high temp silicone oil, Aldrich Chemical Co., Milwaukee, Wis. paraffin oil, Fisher Scientific, Fairlawn, N.J.) in a 0.5 ml eppendorf tube and centrifuged at 13K rpm for 1 min. The tube was frozen in a dry ice-ethanol bath and the bottom cut off for counting. The percentage of specific binding was plotted against the amount of competitor to determine the inhibition curves of each recombinant protein.

In Vivo Half-Life

To saturate the thyroid gland with iodine, mice were given a 0.1 mg/ml solution of KI in place of water for 7 days prior to the assay. The mice were then injected intraperitoneally in triplicate with $5×10^6$ cpm $^{125}$I-labeled Ab and counted in a whole body counter (Wm. B. Johnson & Associates Inc., Ronceverte, W.Va.) over the course of 300 hours, maintaining the 0.1 mg/ml solution of KI throughout. The percentage of the initial counts remaining was plotted against time, and the alpha and beta phase of clearance were calculated from the slope.

Figure 9:
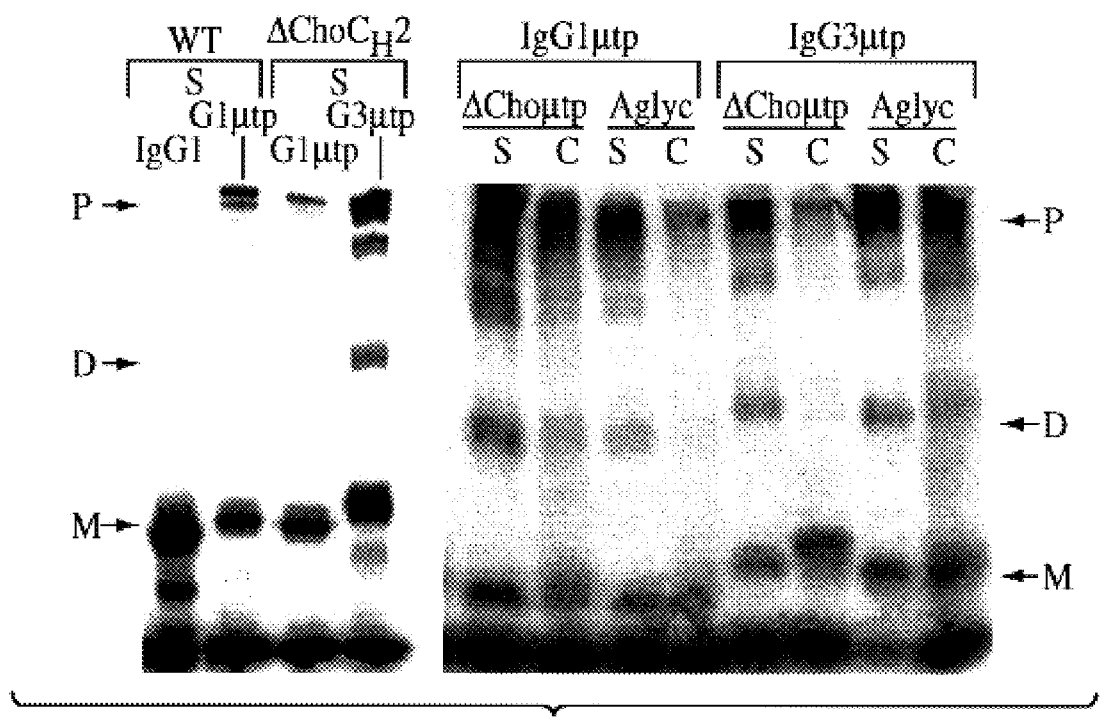
FIG. 9 is a gel showing that mutant and wild type antibodies display similar polymerization patterns. IgG1μtp, IgG1μtpΔChoC$_H$2, IgG1μtpΔChoμtp, IgG1μtpAglyc, IgG3μtp, IgG3μtpΔChoC$_H$2, IgG3μtpΔChoμtp and IgG3μtpAglyc were biosynthetically labeled by overnight growth in medium containing [$^{35}$S] methionine. Cytoplasmic lysates and secretions were prepared and immunoprecipitated using rabbit anti-human Fc+Fab and IgGSorb. The immunoprecipitates were analyzed on 4% tris-glycine SDS gels in the absence of reducing agents. IgG1 is included to mark the position of the $H_2L_2$ monomer form. The position of polymers (P), dimers (D) and monomer (M) is indicated by arrows. Left panel secreted (S) proteins. Right panel secreted (S) and cytoplasmic (C) proteins. ΔChoμtp=Abs. lacking carbohydrate in the tail piece. ΔChoC$_H$2=Abs lacking carbohydrate in C$_H$2. Aglyc=completely aglycosylated Abs. WT=Abs without any mutations.

IgG lacking carbohydrate within $C_H2$ is impaired in its ability to activate complement and to bind Fc receptors (Tao, M. H., and Morrison, S. L., 1989, J. Immunol. 143(8) :2595–601; Tao, M. H. et al., 1993, J. Exper. Med. 178(2) :661–7). Since polymerization of IgG potentiates its ability to perform effector functions, we provided the aglycosylated constant regions of IgG1 and IgG3 with the μtp and determined if they are able to polymerize and if the polymeric forms were able to activate C' and bind Fc receptors. IgG1 and IgG3 with μtp but lacking carbohydrate within $C_H2$ (IgG1μtpΔCho$C_H2$ and IgG3μtpΔCho$C_H2$) were able to form polymers ranging in size from dimers to pentamers/ hexamers with the majority of the antibody secreted as monomer or pentamer/hexamer (FIG. 9).

The N-linked carbohydrate addition site within μtp at Asn563 is homologous to the carbohydrate addition site in αtp at Asn459. Removal of this site in the αtp of IgA prevents the secretion of covalently bound dimers, indicating that a glycan in this position is necessary for appropriate polymer formation (Krugmann, S. et al., 1997, Biochem. Soc. Trans. 25(2):323S). Additionally, the presence of the tail-piece sugar in IgM has been reported to be important for the incorporation of J chain (Wiersma, E. J. et al., 1997, J. Immunol. 158(4):1719–26). However, IgG1μtp and IgG3μtp containing the Asn563 to Gln mutation were able to form polymers of all sizes. IgG1μtp and IgG3μtp lacking both the μtp and $C_H2$ carbohydrates show a similar secretion pattern. Analysis of the mutant IgGs under reduced conditions confirmed that the heavy and light chain were of the expected sizes and that like the IgGμtp polymers they failed to incorporate J chain. Failure to incorporate J chains was confirmed by Western blot analysis of purified proteins.

Figure 10:
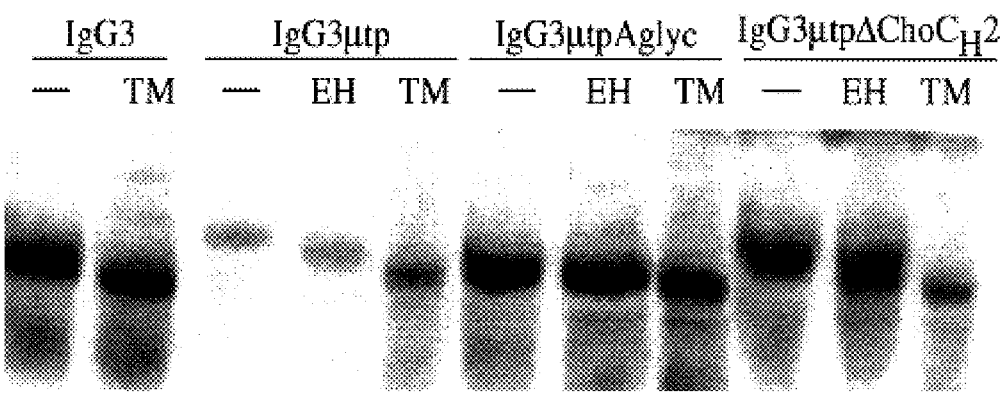
FIG. 10 is a gel showing endoglycosidase H digestion of immunoprecipitated WT and mutant IgG3μtp. Biosynthetically labeled immunoprecipitated antibody was digested with Endo H glycosidase for 24 hours and analyzed in 12% tris glycine reducing SDS PAGE. Untreated and EndoH (EH) treated heavy chains are shown and compared to aglycosylated antibody obtained after treatment of cells with tunicamycin (TM).

To detect unprocessed sugars characteristic of the IgMμtp, immunoprecipitates of radiolabeled IgG3μtp and its carbohydrate mutants were digested with EndoH glycosidase. IgG3μtp was sensitive to EndoH digestion suggesting that the carbohydrate in the μtp is a high mannose sugar although a portion of the heavy chain remains undigested (resistant) (FIG. 10). The IgG3μtp lacking the $C_H2$ carbohydrate but containing the μtp carbohydrate was also only partially sensitive to EndoH digestion. IgG3μtpAglyc which lacks both the $C_H2$ and tail-piece glycosylation sites showed no alterations in size as expected following either EndoH or tunicamycin treatment indicating that it lacks carbohydrate. Therefore the additional potential glycosylation site present at Asn392 in $C_H3$ of IgG3 is not used. Glycosylation at this site may be responsible for the aggregation of murine IgG3 and some rheumatoid factors (Panka, D. J., 1997, Mol. Immunol. 34(8–9):593–8).

Analysis of Complement Activity

Antigen specific aggregation of IgG is an important step in the activation of C' and we previously showed that IgG aggregated through polymerization by addition of a μtp results in C' activation independent of antigen (Smith, R. I. et al., 1995, J. Immunol. 154(5):2226–36). IgG4, normally devoid of C' activation activity, when polymerized acquires this effector function. Therefore, we evaluated the capacity of polymers of aglycosylated IgG1 and IgG3, which do not activate C' in the monomeric form, to interact with the C' system. We measured the ability of Ab complexed to Ag coated microtiter dishes to bind C1q, the initial step of the Classical Cascade. We also analyzed their ability to activate the entire C' cascade as shown by their ability to effect C' mediated lysis of Ag coated target cells. Both assays used normal human serum (NHS) as the C' source.

Figure 11:
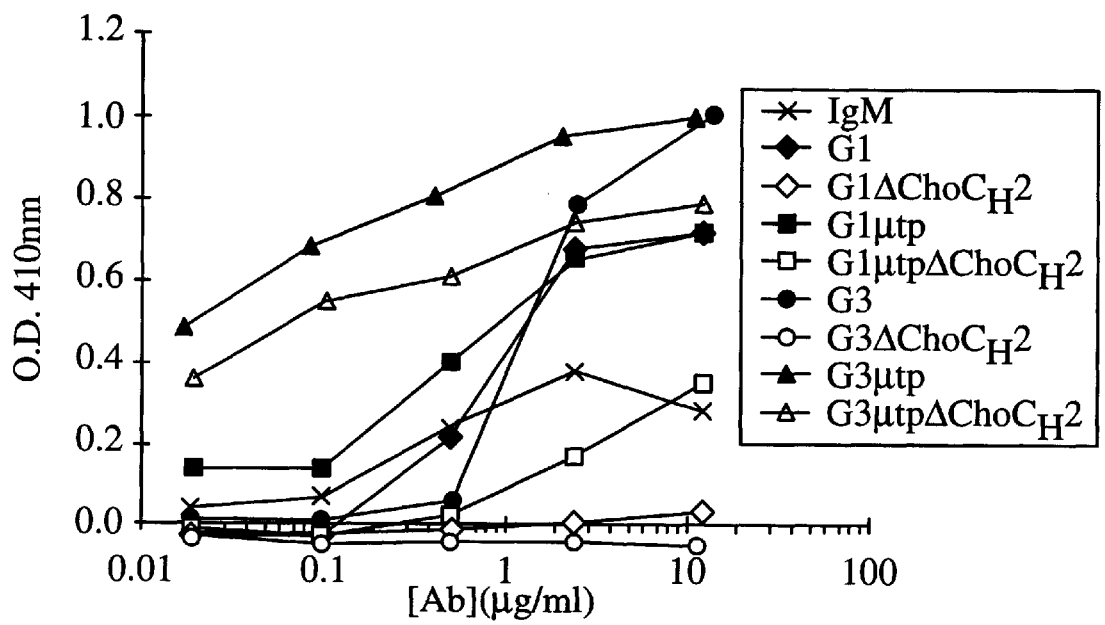
FIG. 11 is a graph showing C1q binding by wild type and mutant IgGs. Antibodies at varying concentrations were added to DNS-BSA-coated microtiter dishes and unbound protein washed away. Preabsorbed NHS, the source of C1q, was then applied to the dish. After washing, goat anti-human C1q was applied. The Ab-C1q complex was then detected by the addition of swine anti-goat IgG-alkaline phosphatase conjugate and subsequent cleavage of the enzyme substrated p-nitrophenyl phosphate. Optical densities at 410 nm were measured on a Dynatech MR700 plate reader.

Polymers of IgG1 and IgG3 aglycosylated in $C_H2$ both bind C1q, albeit they were not as effective as their wild type polymer counterparts, requiring five to ten times more Ab to give the same signal (FIG. 11). However, the mutant polymers show greater ability to bind C1q than the wild type monomers and much higher activity than aglycosylated monomeric Abs, which are negative at all concentrations tested. In all instances, IgG3 was more active than the comparable form of IgG1. Removal of carbohydrate from the μtp had little affect on C1q binding.

Figure 12:
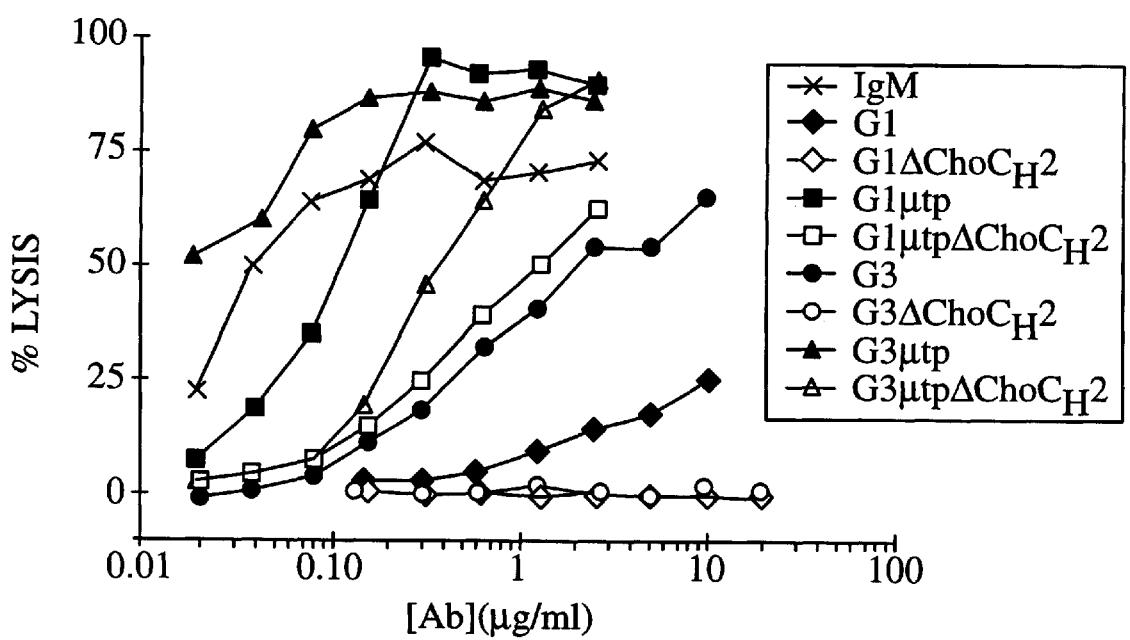
FIG. 12 is a graph showing C' mediated hemolysis by wild and mutant IgG lacking the C$_H$2 carbohydrate. $^{51}$Cr loaded, DNS-BSA coated SRBC were incubated at 37° C. with varying concentrations of antibody in the presence of NHS, preabsorbed against DNS-BSA coated SRBC for 45 min. Unlysed cells were pelleted by centrifugation and the supernatant assayed for released radioactivity. Values are expressed as the percentage of lysis compared with the maximum lysis achieved with $dH_2O$.

Similar results were seen when the ability of antibodies to effect C' mediated hemolysis was evaluated; polymeric IgG1μtp and IgG3μtp lacking carbohydrate in $C_H2$ are able to effect lysis although not as effectively as the wild type polymers (FIG. 12). Completely aglycosylated polymeric IgG was similar to polymers lacking only the $C_H2$ carbohydrate.

Binding to FcgRII

Figure 13:
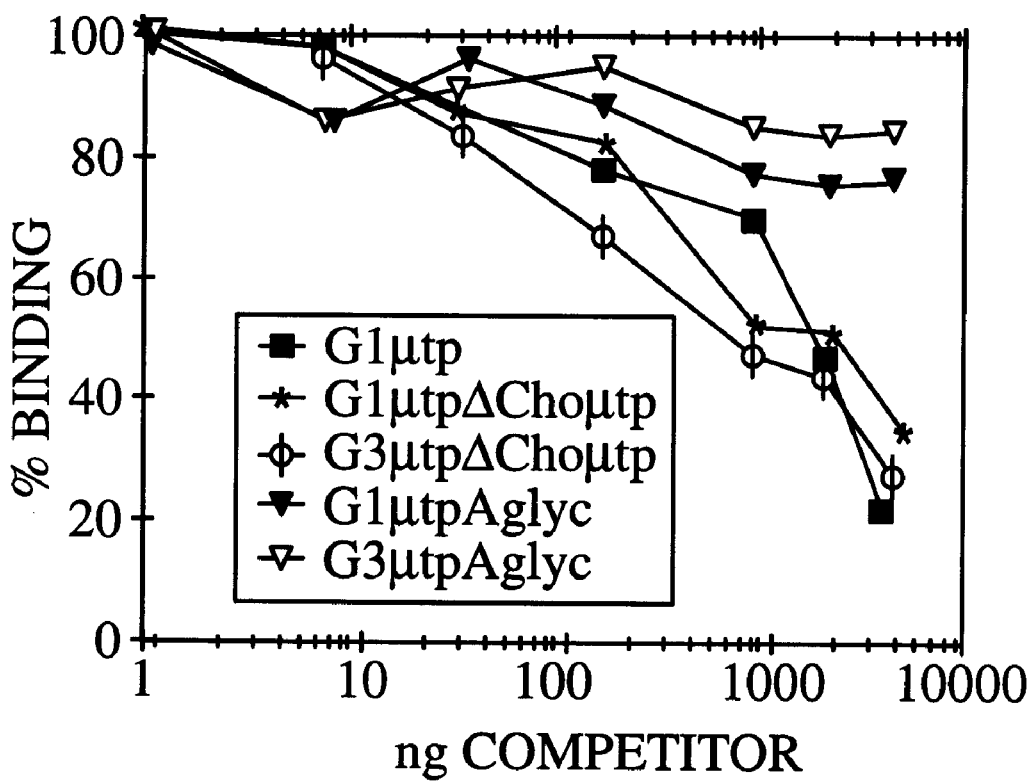
FIG. 13 is a graph showing that antibodies lacking C$_H$2 carbohydrate are impaired in their ability to bind FcR. Increasing concentrations of cold competitor were used to inhibit the binding of $^{125}$I IgG1μtp to FcgRII on K562 cells. Data are plotted as percentage of the maximum binding of $^{125}$I IgG1μtp in the absence of added competitor.

The interaction between the Fc region of monomeric IgG and FcgRII is of low affinity and cannot be detected using monomeric IgG (Lund, J. et al., 1992, Mol. Immunol. 29(1):53–9; Warmerdam, P. et al., 1993, Internat'l Immunol. 5(3):239–47). Polymers of IgG1, IgG3 and IgG4 are able to bind the low affinity receptor. Binding to FcgRII was examined using the multipotential hematopoietic cell line K562. $^{125}$I-labeled IgG1μtp was incubated with cells expressing the receptor in the presence of varying amounts of unlabeled competitor protein and the percentage of added radioactivity bound was determined. Both IgG1μtpΔChoμtp and IgG3μtpΔChoμtp were effective inhibitors, indicating that the carbohydrate in the μtp was not required for FcgRII binding. In contrast completely aglycosylated polymers lost their ability to bind to FcgRII and were unable to inhibit the binding of IgG1μtp (FIG. 13). Similar results were obtained when the mutant polymers were assayed for FcgRI binding using the monocytic cell line U937. Therefore, the presence of carbohydrate in $C_H2$ is critical for IgG1 and IgG3 to bind to FcgRI and FcgRII since even polymeric IgG1 and IgG3 lacking this carbohydrate are unable to bind.

In vivo Half-Life

Figure 14A:
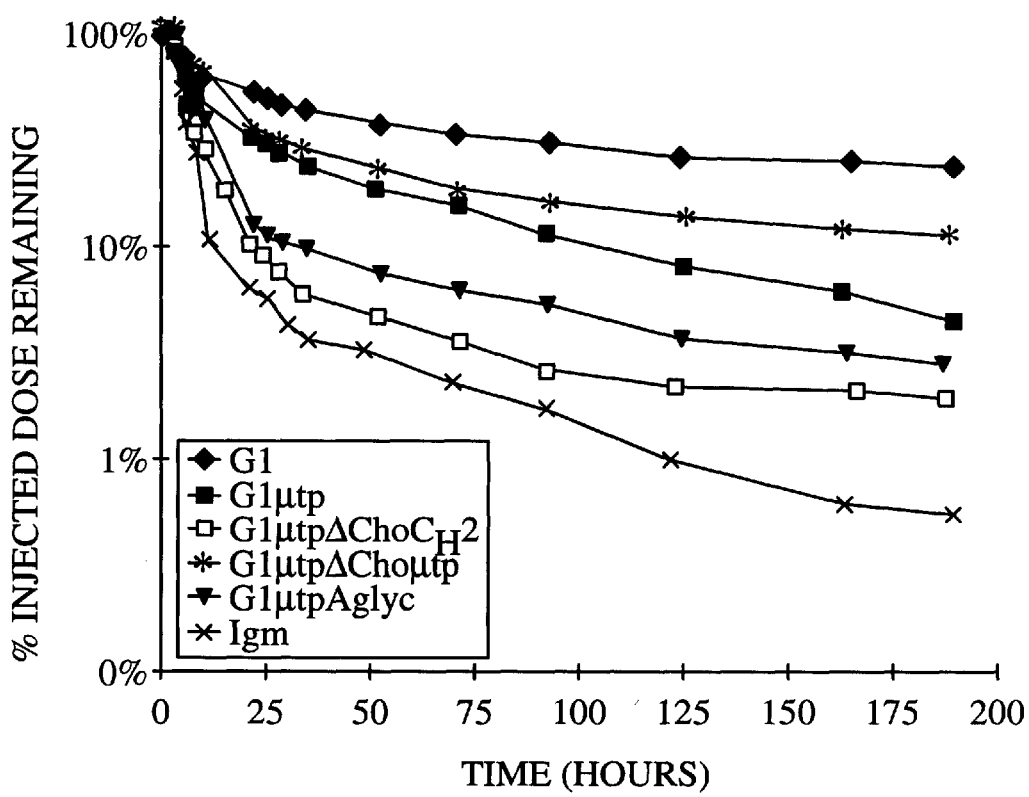
FIG. 14A is a graph showing in vivo half-life of $^{125}$I-labeled Igμtps, in particular, IgG1 polymer and the glycosylation mutants. Mice were injected IP with radiolabelled proteins and the residual radioactivity followed for 300 hours using a whole body counter. Data are plotted as the % cpm remaining of injected dose.
Figure 14B:
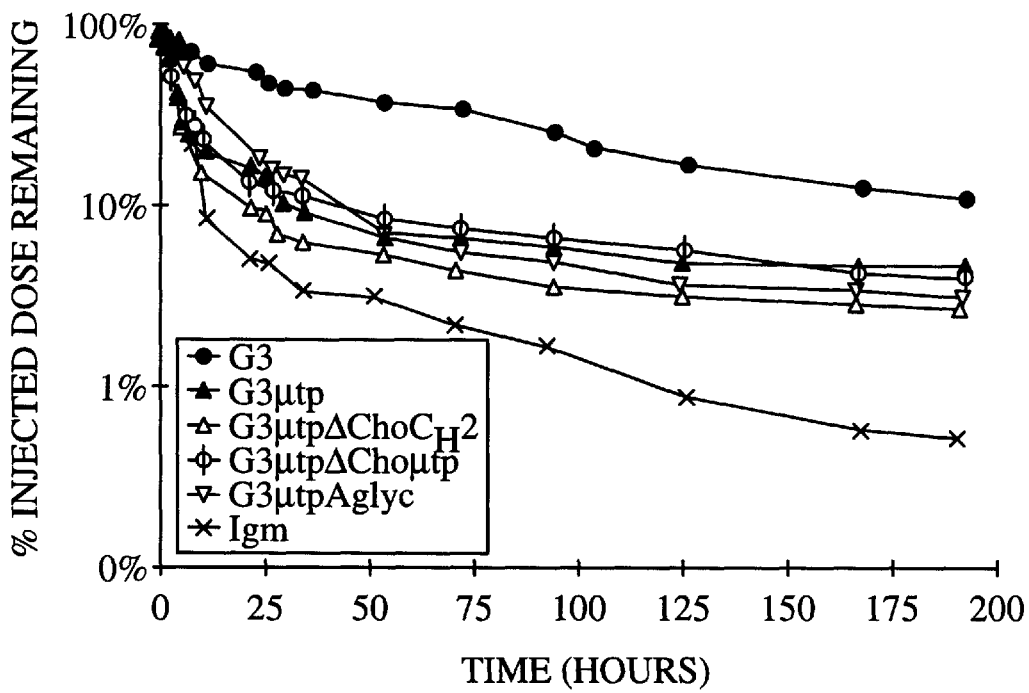
FIG. 14B is a graph showing in vivo half-life of $^{125}$I-labeled Igμtps, in particular, IgG3 polymer and the glycosylation mutants. Mice were injected IP with radiolabelled proteins and the residual radioactivity followed for 300 hours using a whole body counter. Data are plotted as the % cpm remaining of injected dose.

BALB/c mice were injected intraperitoneally with $^{125}$I-labeled antibodies and the radioactivity present in the injected mice determined at various times by whole body counting. As seen before, IgM had a very fast initial clearance with over 90% of the injected protein removed in the first 10 hours with a half-life of 3 hours (FIGS. 14A & 14B). Only 10–20% of the monomeric wild type IgG1 and IgG3 was cleared in the same period of time.

The IgG1 polymers differ in their clearance patterns. Mice injected with IgG1μtpAglyc or IgG1μtpΔCho$C_H2$ cleared 90% of the injected radioactivity by 24 hours, while those injected with IgG1μtp and IgG1ΔChoμtp had cleared only about 50% of the initial radioactivity in the same period. After 24 hours, the clearance of IgG1ΔChoμtp paralleled that of IgG1 while IgG1μtp continued to be more rapidly cleared. The rate of clearance of IgGμtpΔCho$C_H2$ and IgG1μtpAglyc also decreased after 24 hours but this may be due to monomers or other contaminants in the preparation since only a small percentage of the total injected radioactivity remains.

All of the IgG3 polymers cleared 80 to 90% of the injected counts in the first 24 hours. The radioactivity remaining after 24 hours cleared more slowly; however, this may represent residual monomers in the preparation (FIG. 14B).

Upon binding to specific antigens, antibodies interact through their Fc regions with both cellular and soluble effector systems. Despite their similar structure, different human IgG isotypes display differences in the ability to perform effector functions, and these differences are attributed mainly to differences in the lower hinge-$C_H2$ regions.

Extensive studies have localized the binding sites on IgG for C1q and Fc receptors to the $C_H2$ region (Tan, L. K. et al., 1990, PNAS, USA 87(1):162–6; Duncan, A. R., and Winter, G., 1988, Nature 332(6166):738–40). The removal of N-linked carbohydrate from $C_H2$ in wild type monomeric IgG1 and IgG3 results in decreased C1q binding and the elimination of C' activation and recognition by Fc receptors (Tao, M. H., and Morrison, S. L., 1989, J. Immunol. 143(8):2595–601); Coloma, M. J. et al., 1997, J. Immunol. 158(2):733–40; Walker, M. R. et al., 1989, Biochem. J. 259(2):347–53).

Although IgG4 is normally incapable of C' activation (Dangl, J. L. et al., 1988, Embo Journal 7(7):1989–94; Bruggemann, M. et al., 1987, J. Exper. Med. 166(5):1351–61), a multimeric form of IgG4 is capable of C' mediated cytolysis, albeit with reduced efficiency compared to the other gamma isotypes. In this example, we provide a $\mu$tp to IgG1 and IgG3 antibodies lacking carbohydrate in the constant region. Although monomers of IgG1 and IgG3 lacking $C_H2$ carbohydrate are normally devoid of C' activation activity, the resulting polymeric Abs bound C1q almost as efficiently as the wild type polymers and promoted C' mediated lysis of antigen coated cells. Monomeric IgG has low affinity for C1q. For C' activation to occur, there must be formation of Fc arrays capable of simultaneously binding more than one of the six heads on the C1q molecule (Hughes, N. et al., 1984, Eur. J. Immunol. 14(11):974–8). It is possible that IgG lacking the carbohydrate in the constant region has a more rigid structure and that the C1q binding sites are buried or incapable of forming Fc arrays upon binding antigen. Polymerization through the $\mu$tp may produce a conformational change in the constant region allowing the C1q binding sites to be exposed or may facilitate the formation of Fc arrays. Alternatively, antibodies lacking the carbohydrate in $C_H2$ may have a reduced affinity for C1q and polymerization may overcome the low affinity interaction between the Fcs and the first component of the C' system.

We also have removed the carbohydrate in the $\mu$tp by mutating the glycan addition site. Although the tail-piece carbohydrate has previously been reported to be necessary for effective polymerization of IgM and for polymerization and J chain binding by IgA, IgG lacking the glycan in the tail-piece and IgG completely devoid of carbohydrate were still able to form polymers. We also find no evidence for J chain in any of the forms of IgG$\mu$tp; therefore some additional feature required for J chain association present in the constant region of IgM is lacking in IgG.

Antibodies trigger cellular mechanisms through Fcg receptors displayed on their surface. While aglycosylated polymers retained the ability to activate C', they lose the ability to bind to the high affinity FcgRI and low affinity FcgRII receptors, indicating either that the sugar is part of the binding site or contributes to its proper conformation. The fact that polymerization did not lead to binding, suggests that the site required for FcR binding is absent and not merely of low affinity. The ability of the aglycosylated polymeric IgGs to activate complement but not bind to FcgRs confirms that the sites recognized by C1q and the FcgRs differ.

Although the rapid clearance of IgG polymers resembles the clearance pattern of IgM and not of IgG, the IgG mutant polymers do not clear as rapidly as IgM. Since IgG$\mu$tps do not contain J chain, its presence is not responsible for the rapid removal of the polymers. The lack of carbohydrate in $C_H2$ accelerates clearance for polymers of IgG1. This is in contrast to what was observed with monomeric IgG in which removal of the $C_H2$ carbohydrate in IgG1 did not influence serum half-life (Tao, M. H. et al., 1993, J. Exper. Med. 178(2):661–7). In vivo persistence of IgG is determined at least in part by binding to the Brambell receptor, FcRn (Junghans, R., 1997, Immunol. Res. 16(1):29–57; Ravetch, J., 1997, Curr. Opin. Immunol. 9(1):121–5). Removal of the constant region carbohydrate would not be expected to alter binding to that receptor. The removal of the $\mu$tp carbohydrate appears to increase the half life of polymeric IgG1. The differences observed among the different mutant species could be influenced by the in vivo stability of the protein and/or the different rates of conversion to monomeric forms.

These examples have shown that while the tail-pieces from IgA and IgM are similar, they exhibit similar functions in some but not all contexts. Addition of either tail-piece to IgG results in the secretion of polymers ranging in size up to hexamers. Therefore there is nothing inherent in the sequence of the $\alpha$tp that limits the polymerization state of IgA predominantly to dimers. IgA with the $\mu$tp and IgM with the $\alpha$tp are both impaired in their ability to incorporate J chain suggesting that the sequence of the tail-piece can influence the ability of polymeric Igs to form covalent bonds with J chain. We have confirmed that the presence of carbohydrate in the constant region of polymeric IgG1 and IgG3 is essential for their ability to bind to Fc receptors.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A modified immunoglobulin molecule consisting essentially of one or more heavy chains from the constant domain of an IgA molecule, and at least a portion of a nonIgA immunoglobulin molecule, wherein the one or more IgA heavy chains are selected from the group consisting of a $C_H1$ domain, a hinge domain, a $C_H2$ domain, and a $C_H3$ domain and does not include a complete Fc region.

2. The modified immunoglobulin molecule of claim 1, wherein the portion of a nonIgA immunoglobulin molecule comprises a $C_H1$ domain.

3. The modified immunoglobulin molecule of claim 1, wherein the portion of a nonIgA immunoglobulin molecule comprises a $C_H3$ domain.

4. The modified immunoglobulin molecule of claim 1, wherein the portion of a nonIgA immunoglobulin molecule comprises a $C_H2$ domain.

5. The modified immunoglobulin molecule of claim 1, wherein the IgA is IgA1 or IgA2.

6. The modified immunoglobulin molecule of claim 1, further comprising an antigen-binding region.

7. The modified immunoglobulin molecule of claim 1, wherein the nonIgA immunoglobulin molecule is an IgG, IgM, IgE, or IgD molecule.

8. The modified immunoglobulin molecule of claim 7, wherein the nonIgA immunoglobulin molecule is an IgG molecule.

9. The modified immunoglobulin molecule of claim 1, further comprising a tail-piece region of an IgA immunoglobulin molecule.

10. The modified immunoglobulin molecule of claim 1, further comprising a tail-piece region of a nonIgA immunoglobulin molecule.

11. The modified immunoglobulin molecule of claim 1, further comprising J chain.

12. The modified immunoglobulin molecule of claim 1, further comprising secretory component (SC).

13. The modified immunoglobulin molecule of claim 1, wherein a carbohydrate addition site has been deleted.

14. The modified immunoglobulin molecule of claim 10, wherein a carbohydrate addition site is deleted from the tail-piece region.

15. A polynucleotide that encodes a modified immunoglobulin molecule of claim 1.

16. A vector comprising the polynucleotide of claim 1.

17. A host cell transfected with the vector of claim 16.

18. A method of producing a modified immunoglobulin molecule comprising culturing the host cell of claim 17, and recovering the modified immunoglobulin molecule so produced.

19. The method of claim 18, wherein the cell is a eucaryotic or procaryotic cell.

20. The method of claim 18, wherein the cell is a mammalian, avian, reptilian, insect, plant, bacterial, or yeast cell.

21. The method of claim 20, wherein the mammalian cell is a human, rabbit, murine, rat, or bovine cell.

22. The method of claim 18, wherein the host cell is a myeloma cell, Sp2/0 cell, CHO cell, L cell, COS cell, fibroblast, MDCK cell, HT29 cell or a T84 cell.

23. A pharmaceutical composition comprising the modified immunoglobulin molecule of claim 1 and a pharmaceutically acceptable carrier.

24. A method of treating or protecting against an infection in a subject comprising administering the composition of claim 23 to the subject.

25. The method of claim 24, wherein the infection is systemic, local, or at a mucosal surface.

26. The method of claim 24, wherein the infection is a bacterial, viral, mycoplasmal, mycobacterial, yeast, or parasitic infection.

27. The method of claim 26, wherein the viral infection is a human immunodeficiency virus, hepatitis virus, respiratory syncytial virus, influenza virus, or cold virus infection.

28. The method of claim 24 wherein the subject is a mammal, bird, reptile, or fish.

29. The method of claim 28, wherein the mammal is a primate.

30. The method of claim 29, wherein the primate is human.

31. The modified immunoglobulin molecule of claim 4, further comprising a hinge domain of an IgA molecule.

* * * * *

UNITED STATES PATENT AND TRADEMARK OFFICE
CERTIFICATE OF CORRECTION

PATENT NO.   : 6,284,536 B1
DATED        : September 4, 2001
INVENTOR(S)  : Sherie L. Morrison et al.

It is certified that error appears in the above-identified patent and that said Letters Patent is hereby corrected as shown below:

<u>Title page, Item [54] and Column 1, line 1,</u>
"IMMUNOGLOBIN" should read -- IMMUNOGLOBULIN --.

Signed and Sealed this

Eleventh Day of February, 2003

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 23
<212> TYPE: DNA
<213> ORGANISM: homo sapiens

<400> SEQUENCE: 1
ccgctgcgcg ggtaaaccca ccc     23

```
<210> SEQ ID NO 2
<211> LENGTH: 22
<212> TYPE: DNA
<213> ORGANISM: homo sapiens

<400> SEQUENCE: 2
ctggatcccc ccctcctgca cc                                              22

<210> SEQ ID NO 3
<211> LENGTH: 23
<212> TYPE: DNA
<213> ORGANISM: homo sapiens

<400> SEQUENCE: 3
ccgctgcgca ggtaaaccca ccc                                             23

<210> SEQ ID NO 4
<211> LENGTH: 22
<212> TYPE: DNA
<213> ORGANISM: homo sapiens

<400> SEQUENCE: 4
ctggatcccc ccctcctgca cc                                              22

<210> SEQ ID NO 5
<211> LENGTH: 22
<212> TYPE: DNA
<213> ORGANISM: homo sapiens

<400> SEQUENCE: 5
cacagccccg gggtgcccac ca                                              22

<210> SEQ ID NO 6
<211> LENGTH: 23
<212> TYPE: DNA
<213> ORGANISM: homo sapiens

<400> SEQUENCE: 6
ggtgggtttg ccggccaagc ggt                                             23

<210> SEQ ID NO 7
<211> LENGTH: 22
<212> TYPE: DNA
<213> ORGANISM: homo sapiens

<400> SEQUENCE: 7
aactagtgga tcccccctc ct                                               22
```